(12) United States Patent
Gregerson et al.

(10) Patent No.: US 12,207,892 B2
(45) Date of Patent: Jan. 28, 2025

(54) INTEGRATED MEDICAL IMAGING AND SURGICAL ROBOTIC SYSTEM

(71) Applicant: Mobius Imaging, LLC, Shirley, MA (US)

(72) Inventors: Eugene A. Gregerson, Bolton, MA (US); Paul Sebring, Townsend, MA (US); Russell Stanton, Lunenberg, MA (US); Scott Coppen, Amesbury, MA (US); Adeline Harris, Grass Valley, CA (US); Todd Furlong, Goffstown, NH (US); Jeff Baker, Goffstown, NH (US)

(73) Assignee: Mobius Imaging, LLC, Shirley, MA (US)

( * ) Notice: Subject to any disclaimer, the term of this patent is extended or adjusted under 35 U.S.C. 154(b) by 0 days.

(21) Appl. No.: 18/388,029

(22) Filed: Nov. 8, 2023

(65) Prior Publication Data
US 2024/0065777 A1 Feb. 29, 2024

Related U.S. Application Data

(63) Continuation of application No. 17/131,386, filed on Dec. 22, 2020, now Pat. No. 11,857,269, which is a
(Continued)

(51) Int. Cl.
*A61B 5/05* (2021.01)
*A61B 5/00* (2006.01)
(Continued)

(52) U.S. Cl.
CPC ............ *A61B 34/20* (2016.02); *A61B 5/0036* (2018.08); *A61B 5/055* (2013.01); *A61B 6/12* (2013.01);
(Continued)

(58) Field of Classification Search
CPC ......... A61B 34/20; A61B 34/30; A61B 5/055; A61B 5/0036; A61B 2090/2055;
(Continued)

(56) References Cited

U.S. PATENT DOCUMENTS

| 5,799,055 A | 8/1998 | Peshkin et al. |
| 5,921,992 A | 7/1999 | Costales et al. |

(Continued)

FOREIGN PATENT DOCUMENTS

| CA | 2948719 A1 | 9/2014 |
| CN | 1668246 A | 9/2005 |

(Continued)

OTHER PUBLICATIONS

Communication Pursuant to Rules 70(2) and 70a(2) EPC in related Application No. EP 16780883.1-1124/3282997 in related PCT Application No. PCT/US2016/027860 dated Jan. 7, 2019.
(Continued)

*Primary Examiner* — Joel F Brutus
(74) *Attorney, Agent, or Firm* — Howard & Howard Attorneys PLLC

(57) ABSTRACT

Methods and systems for performing robotically-assisted surgery in conjunction with intra-operative imaging. A method includes moving a robotic arm with respect to a patient and an imaging device to move an end effector of the robotic arm to a pre-determined position and orientation with respect to the patient based on imaging data of the patient obtained by the imaging device. The robotic arm maintains the end effector in the pre-determined position and orientation with respect to the patient and does not collide with the imaging device or with the patient when the imaging device moves with respect to the patient.

20 Claims, 36 Drawing Sheets

Related U.S. Application Data continuation of application No. 15/130,258, filed on Apr. 15, 2016, now Pat. No. 10,959,783.

(60) Provisional application No. 62/147,924, filed on Apr. 15, 2015.

(51) Int. Cl.

| | | |
|---|---|---|
| *A61B 5/055* | (2006.01) | |
| *A61B 6/00* | (2006.01) | |
| *A61B 6/12* | (2006.01) | |
| *A61B 34/20* | (2016.01) | |
| *A61B 34/30* | (2016.01) | |
| *A61B 46/10* | (2016.01) | |
| *A61B 90/00* | (2016.01) | |
| *A61B 5/06* | (2006.01) | |
| *A61B 5/11* | (2006.01) | |
| *A61B 6/03* | (2006.01) | |
| *A61B 6/04* | (2006.01) | |
| *A61B 8/08* | (2006.01) | |

(52) U.S. Cl.
CPC .............. *A61B 6/547* (2013.01); *A61B 34/30* (2016.02); *A61B 46/10* (2016.02); *A61B 90/37* (2016.02); *A61B 90/39* (2016.02); *A61B 5/064* (2013.01); *A61B 5/1114* (2013.01); *A61B 5/1127* (2013.01); *A61B 6/032* (2013.01); *A61B 6/037* (2013.01); *A61B 6/04* (2013.01); *A61B 6/4441* (2013.01); *A61B 6/4447* (2013.01); *A61B 6/5264* (2013.01); *A61B 8/0841* (2013.01); *A61B 2034/2055* (2016.02); *A61B 2090/376* (2016.02); *A61B 2090/3762* (2016.02); *A61B 2090/3937* (2016.02); *A61B 2505/05* (2013.01)

(58) Field of Classification Search
CPC ...... A61B 2090/326; A61B 2090/3762; A61B 6/032; A61B 6/037; A61B 6/04; A61B 6/4441; A61B 6/12; A61B 6/547
See application file for complete search history.

(56) References Cited

U.S. PATENT DOCUMENTS

| | | | |
|---|---|---|---|
| 6,149,592 | A | 11/2000 | Yanof et al. |
| 6,236,875 | B1 | 5/2001 | Bucholz et al. |
| 6,275,725 | B1 | 8/2001 | Cosman |
| 6,484,049 | B1 | 11/2002 | Seeley et al. |
| 6,533,455 | B2 | 3/2003 | Graumann et al. |
| 6,772,002 | B2 | 8/2004 | Schmidt et al. |
| 6,785,572 | B2 | 8/2004 | Yanof et al. |
| 7,194,120 | B2 | 3/2007 | Wicker et al. |
| 7,251,522 | B2 | 7/2007 | Essenreiter et al. |
| 7,587,235 | B2 | 9/2009 | Wist et al. |
| 7,699,877 | B2 | 4/2010 | Davison |
| 7,722,530 | B2 | 5/2010 | Davison |
| 7,799,036 | B2 | 9/2010 | Davison et al. |
| 8,016,835 | B2 | 9/2011 | Birkmeyer et al. |
| 8,046,054 | B2 | 10/2011 | Kim et al. |
| 8,118,488 | B2 | 2/2012 | Gregerson |
| 8,126,114 | B2 | 2/2012 | Naylor et al. |
| 8,308,361 | B2 | 11/2012 | Gregerson et al. |
| 8,394,144 | B2 | 3/2013 | Zehavi et al. |
| 8,454,583 | B2 | 6/2013 | Perez-Cruet et al. |
| 8,457,790 | B2 | 6/2013 | Blondel et al. |
| 8,509,503 | B2 | 8/2013 | Nahum et al. |
| 8,761,337 | B2 | 6/2014 | Naylor et al. |
| 8,795,188 | B2 | 8/2014 | Maschke |
| 8,974,460 | B2 | 3/2015 | De la Fuente Klein et al. |
| 9,125,680 | B2 | 9/2015 | Kostrzewski et al. |
| 9,237,861 | B2 | 1/2016 | Nahum et al. |
| 9,259,282 | B2 | 2/2016 | Azizian et al. |
| 9,283,048 | B2 | 3/2016 | Kostrzewski et al. |
| 9,308,050 | B2 | 4/2016 | Kostrzewski et al. |
| 9,545,233 | B2 | 1/2017 | Sirpad et al. |
| 9,550,299 | B2 | 1/2017 | Wolf et al. |
| 9,750,432 | B2 | 9/2017 | Nahum et al. |
| 9,833,292 | B2 | 12/2017 | Kostrzewski et al. |
| 10,004,562 | B2 | 6/2018 | Kostrzewski et al. |
| 10,039,476 | B2 | 8/2018 | Nahum et al. |
| 10,064,682 | B2 | 9/2018 | Azizian et al. |
| 10,076,385 | B2 | 9/2018 | Shoham et al. |
| 10,136,948 | B2 | 11/2018 | Jensen |
| 10,136,952 | B2 | 11/2018 | Couture et al. |
| 10,159,534 | B2 | 12/2018 | Maillet et al. |
| 10,549,122 | B2 | 2/2020 | Cheng et al. |
| 10,772,577 | B2 | 9/2020 | Fortuna et al. |
| 10,959,783 | B2 | 3/2021 | Gregerson et al. |
| 11,013,480 | B2 | 5/2021 | Popovic et al. |
| 2003/0097060 | A1 | 5/2003 | Yanof et al. |
| 2004/0170254 | A1 | 9/2004 | Gregerson et al. |
| 2006/0149147 | A1 | 7/2006 | Yanof |
| 2007/0156157 | A1 | 7/2007 | Nahum et al. |
| 2008/0125649 | A1 | 5/2008 | Meyer et al. |
| 2008/0247506 | A1 | 10/2008 | Maschke |
| 2009/0326322 | A1 | 12/2009 | Diolaiti |
| 2009/0326552 | A1 | 12/2009 | Diolaiti |
| 2009/0326553 | A1 | 12/2009 | Mustufa et al. |
| 2010/0172468 | A1 | 7/2010 | Gregerson |
| 2010/0193698 | A1 | 8/2010 | Hassan |
| 2011/0276179 | A1 | 11/2011 | Banks et al. |
| 2012/0035470 | A1* | 2/2012 | Kuduvalli .............. A61B 6/032 600/427 |
| 2012/0190981 | A1 | 7/2012 | Harris et al. |
| 2013/0085510 | A1* | 4/2013 | Stefanchik ............ A61B 34/30 901/30 |
| 2013/0158565 | A1* | 6/2013 | Anvari ................... A61B 90/00 606/130 |
| 2014/0003572 | A1 | 1/2014 | Gregerson et al. |
| 2014/0046212 | A1* | 2/2014 | Deutschmann ...... A61B 6/0407 378/20 |
| 2014/0049629 | A1 | 2/2014 | Siewerdsen et al. |
| 2014/0139215 | A1 | 5/2014 | Gregerson et al. |
| 2014/0163736 | A1 | 6/2014 | Azizian et al. |
| 2014/0188132 | A1* | 7/2014 | Kang ................... A61B 6/4441 606/130 |
| 2014/0222023 | A1 | 8/2014 | Kim et al. |
| 2014/0249546 | A1 | 9/2014 | Shvartsberg et al. |
| 2014/0265182 | A1 | 9/2014 | Stanton et al. |
| 2014/0275953 | A1 | 9/2014 | Gregerson et al. |
| 2014/0275955 | A1 | 9/2014 | Crawford et al. |
| 2014/0316430 | A1 | 10/2014 | Hourtash |
| 2014/0343421 | A1 | 11/2014 | Kim et al. |
| 2015/0036799 | A1* | 2/2015 | Zhang ................. A61B 6/4014 378/62 |
| 2015/0047452 | A1 | 2/2015 | Wolf et al. |
| 2015/0202009 | A1 | 7/2015 | Nussbaumer et al. |
| 2015/0366624 | A1 | 12/2015 | Kostrzewski et al. |
| 2016/0030117 | A1 | 2/2016 | Mewes |
| 2016/0081754 | A1 | 3/2016 | Kostrzewski et al. |
| 2016/0174914 | A1 | 6/2016 | Lerch et al. |
| 2016/0220320 | A1 | 8/2016 | Crawford et al. |
| 2016/0235492 | A1 | 8/2016 | Morard et al. |
| 2016/0278875 | A1 | 9/2016 | Crawford et al. |
| 2016/0302871 | A1 | 10/2016 | Gregerson et al. |
| 2017/0071691 | A1 | 3/2017 | Crawford et al. |
| 2017/0079727 | A1 | 3/2017 | Crawford et al. |
| 2017/0172669 | A1 | 6/2017 | Berkowitz et al. |
| 2017/0231702 | A1 | 8/2017 | Crawford et al. |
| 2017/0239002 | A1 | 8/2017 | Crawford et al. |
| 2017/0239003 | A1 | 8/2017 | Crawford et al. |
| 2017/0239006 | A1 | 8/2017 | Crawford et al. |
| 2017/0245951 | A1 | 8/2017 | Crawford et al. |
| 2017/0252112 | A1 | 9/2017 | Crawford et al. |
| 2017/0258533 | A1 | 9/2017 | Crawford et al. |
| 2017/0258535 | A1 | 9/2017 | Crawford et al. |
| 2017/0312039 | A1 | 11/2017 | Crawford et al. |
| 2017/0348061 | A1 | 12/2017 | Joshi et al. |
| 2017/0360513 | A1 | 12/2017 | Amiot et al. |
| 2017/0360517 | A1 | 12/2017 | Crawford et al. |
| 2018/0000546 | A1 | 1/2018 | Crawford et al. |

(56) References Cited

U.S. PATENT DOCUMENTS

| | | |
|---|---|---|
| 2018/0110573 A1 | 4/2018 | Kostrzewski |
| 2018/0116739 A1 | 5/2018 | Gogarty et al. |
| 2018/0116740 A1 | 5/2018 | Gogarty et al. |
| 2018/0125597 A1 | 5/2018 | Gogarty et al. |
| 2018/0157238 A1 | 6/2018 | Gogarty et al. |
| 2018/0221098 A1 | 8/2018 | Forsyth et al. |
| 2018/0235715 A1 | 8/2018 | Amiot et al. |
| 2018/0250077 A1 | 9/2018 | Xu et al. |
| 2018/0256259 A1 | 9/2018 | Crawford |
| 2018/0271605 A1 | 9/2018 | Kostrzewski et al. |
| 2018/0346008 A1 | 12/2018 | Nahum et al. |
| 2019/0000561 A1 | 1/2019 | Decker et al. |
| 2019/0000569 A1 | 1/2019 | Crawford et al. |
| 2019/0021795 A1 | 1/2019 | Crawford et al. |
| 2019/0021799 A1 | 1/2019 | Crawford et al. |
| 2019/0021800 A1 | 1/2019 | Crawford et al. |
| 2019/0029759 A1 | 1/2019 | McDonell |
| 2019/0029765 A1 | 1/2019 | Crawford et al. |
| 2019/0038362 A1 | 2/2019 | Nash et al. |
| 2019/0053859 A1 | 2/2019 | Couture et al. |
| 2019/0069961 A1 | 3/2019 | Smith et al. |
| 2019/0099222 A1 | 4/2019 | Nahum et al. |
| 2019/0117313 A1 | 4/2019 | Crawford |
| 2019/0142533 A1 | 5/2019 | Itkowitz et al. |
| 2019/0239964 A1 | 8/2019 | LeBoeuf et al. |
| 2019/0269467 A1 | 9/2019 | Forsyth et al. |
| 2019/0274765 A1 | 9/2019 | Crawford et al. |
| 2021/0106391 A1 | 4/2021 | Gregerson et al. |

FOREIGN PATENT DOCUMENTS

| | | |
|---|---|---|
| CN | 1894577 A | 1/2007 |
| CN | 201422918 Y | 3/2010 |
| CN | 201542641 U | 8/2010 |
| CN | 101700184 B | 1/2011 |
| CN | 101579269 B | 4/2011 |
| CN | 101853333 B | 11/2012 |
| CN | 104185446 A | 12/2014 |
| CN | 104411248 A | 3/2015 |
| EP | 0930046 A2 | 7/1999 |
| WO | 2005046499 A2 | 5/2005 |
| WO | 2015115809 A1 | 8/2015 |
| WO | 2015135057 A1 | 9/2015 |
| WO | 2017036340 A1 | 3/2017 |
| WO | 2017122202 A1 | 7/2017 |
| WO | 2018185729 A1 | 10/2018 |

OTHER PUBLICATIONS

English language abstract and machine-assisted English translation for CN 101579269 extracted from espacenet.com database on Jan. 9, 2020, 8 pages.

English language abstract and machine-assisted English translation for CN 101700184 extracted from espacenet.com database on Jan. 9, 2020, 10 pages.

English language abstract and machine-assisted English translation for CN 101853333 extracted from espacenet.com database on Jan. 9, 2020, 9 pages.

English language abstract and machine-assisted English translation for CN 201422918 extracted from espacenet. com database on Jan. 9, 2020, 7 pages.

English language abstract and machine-assisted English translation for CN 201542641 extracted from espacenet.com database on Jan. 9, 2020, 10 pages.

English language abstract and machine-assisted English translation for WO 2015/115809 extracted from espacenet. com database on Jan. 9, 2020, 8 pages.

English language abstract for WO 2017/036340 extracted from espacenet.com database on Jan. 9, 2020, 2 pages.

English Translation of Relevant Portion of: Wu Ruixiang, "Robot Technology and Application" Beijing University of Aeronautics and Astronautics Press, Aug. 31, 1994, p. 30, provided by NTD Patent and Trademark Agency Limited on Aug. 7, 2020, 1 page.

Extended European Search Report from the European Patent Office in related Application No. EP 16780883.1-1124/3282997 in related PCT Application No. PCT/US2016/027860 dated Dec. 10, 2018.

International Preliminary Report on Patentability for International Application No. PCT/US2016/027860, issued Oct. 26, 2017.

International Search Report and the Written Opinion of the Intenational Searching Authority received from the Korean Intellectual Property Office in International Application No. PCT/US2016/027860 dated Jul. 28, 2016.

PAL jug, Eric et al. "The JPL Serpentine Robot: a 12 DOF System for Inspection", NASA JPL Technical Reports Server, https://trs.jpl.nasa.gov/handle/2014/29159, Jan. 1, 1995, 5 pages.

English language abstract for CN 104185446 A extracted from espacenet.com database on Feb. 21, 2024, 2 pages.

English language abstract for CN 1894577 A extracted from espacenet. com database on Feb. 21, 2024, 2 pages.

English language abstract for CN 1668246 A extracted from espacenet. com database on Feb. 21, 2024, 1 page.

English language abstract for CN 104411248 A extracted from espacenet.com database on May 28, 2024, 2 pages.

\* cited by examiner

INTEGRATED MEDICAL IMAGING AND SURGICAL ROBOTIC SYSTEM

CROSS-REFERENCE TO RELATED APPLICATIONS

This application is a Continuation of U.S. patent application Ser. No. 17/131,386 filed on Dec. 22, 2020, which is a Continuation of U.S. patent application Ser. No. 15/130,258 filed on Apr. 15, 2016 and issued as U.S. Pat. No. 10,959,783 on Mar. 30, 2021, which claims benefit of U.S. Provisional Application No. 62/147,924 filed on Apr. 15, 2015, the entire contents of each of which are incorporated herein by reference.

BACKGROUND OF THE INVENTION

Surgical procedures, such as minimally-invasive procedures, may require a surgeon to insert surgical tools inside the body of the patient to a particular depth to reach the target area inside the patient's body. This can be a challenging and time consuming process. Surgeons may utilize pre-operative diagnostic images (e.g., x-ray CT, MRI) to help guide the surgical tools to the correct location and depth in the body without damaging other tissue or organs of the patient. However, there is still the possibility of inaccuracies in the insertion and placement of the tools, which may result in tools being guided to an incorrect position in the body and/or causing injury or damage to other portions of the patient's anatomy. To avoid such problems, a surgeon may opt to perform a more invasive procedure than might otherwise be necessary. However, this may substantially increase the time and cost of the procedure, and may also increase blood loss, pain and recovery time for the patient.

BRIEF SUMMARY OF THE INVENTION

Various embodiments include methods and systems for performing robotically-assisted surgery. In one embodiment, a method of performing robotically-assisted surgery includes moving a robotic arm with respect to a patient and an imaging device to move an end effector of the robotic arm to a pre-determined position and orientation with respect to the patient based on IMAGING data of the patient obtained by the imaging device, where the robotic arm maintains the end effector in the pre-determined position and orientation with respect to the patient and does not collide with the imaging device or with the patient when the imaging device moves with respect to the patient.

Embodiments may further include determining that the imaging device is moving with respect to the patient and moving the robotic arm to maintain the end effector in the pre-determined position and orientation with respect to the patient while preventing the robotic arm from colliding with the imaging device or with the patient while the imaging device moves with respect to the patient.

Further embodiments include systems for performing robotically-assisted surgery that include a patient support, an imaging device that is movable with respect to the patient support to obtain imaging data of a patient positioned on the patient support, a robotic arm configured to move an end effector of the robotic arm to a pre-determined position and orientation with respect to the patient positioned on the patient support based on imaging data obtained by the imaging device, and a motion tracking apparatus including a camera attached to the imaging device or to the patient support, where the camera is positioned to track the position of one or more objects in a surgical area. In embodiments, the camera may move independently of the imaging device and the patient support to maintain the surgical area within the field of view of the camera.

Further embodiments include a system for performing robotically-assisted surgery that includes an x-ray imaging device including an x-ray source and an x-ray detector mounted to a support structure such that at least one of the x-ray source and the x-ray detector is configured to rotate with respect to the support structure to obtain x-ray images from different projection angles relative to an object being imaged, and a robotic arm having a first end configured to extend into an imaging area between the source and the detector and a second end attached to the support structure.

Further embodiments include a computing device including a processor configured with processor-executable instructions to perform operations of the embodiment methods described above. Further embodiments include a non-transitory processor-readable storage medium having stored thereon processor-executable software instructions configured to cause a processor to perform operations of the embodiment methods described above. Further embodiments include a computing device that includes means for performing functions of the operations of the embodiment methods described above.

BRIEF DESCRIPTION OF THE DRAWINGS

Other features and advantages of the present invention will be apparent from the following detailed description of the invention, taken in conjunction with the accompanying drawings of which.

Figure 6A:
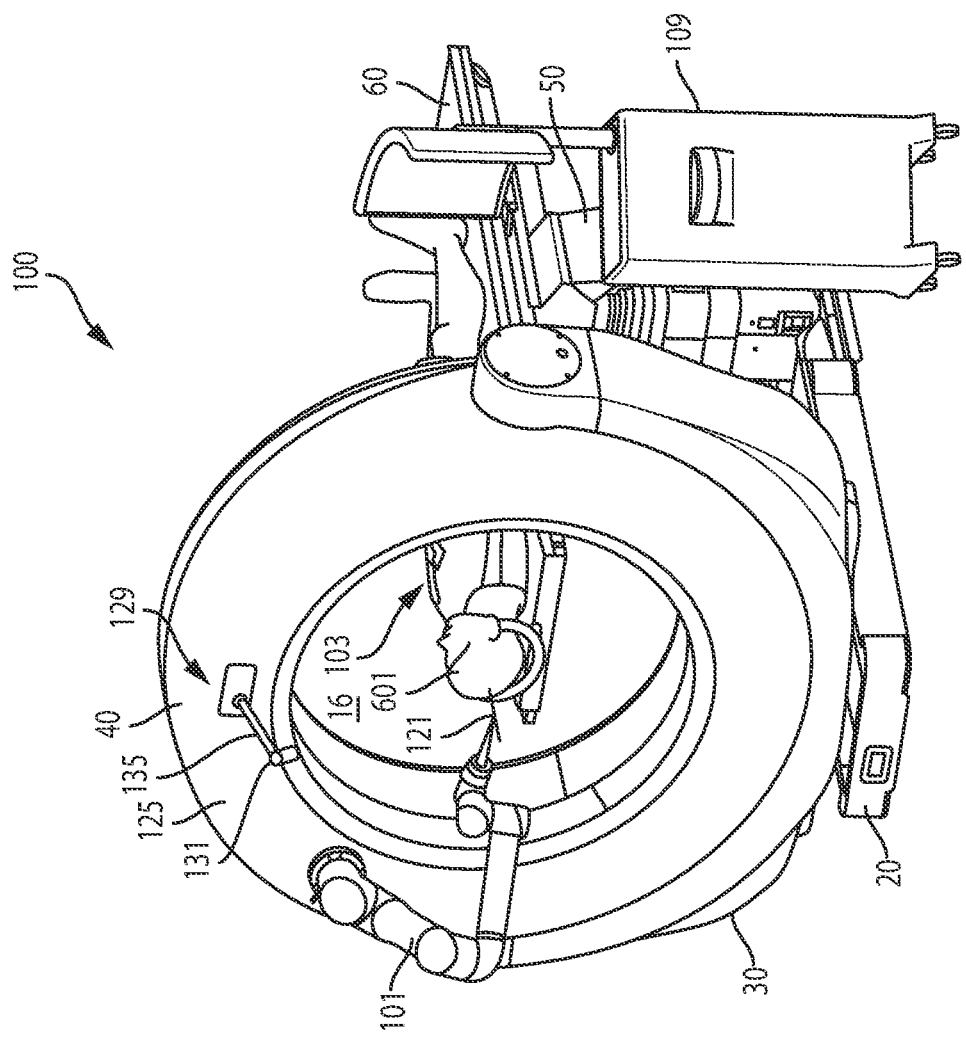
FIGS. 6A-6C are perspective views of a system for performing robotically-assisted surgery having a robotic arm attached to a side of an imaging gantry facing away from the patient.
Figure 6B:
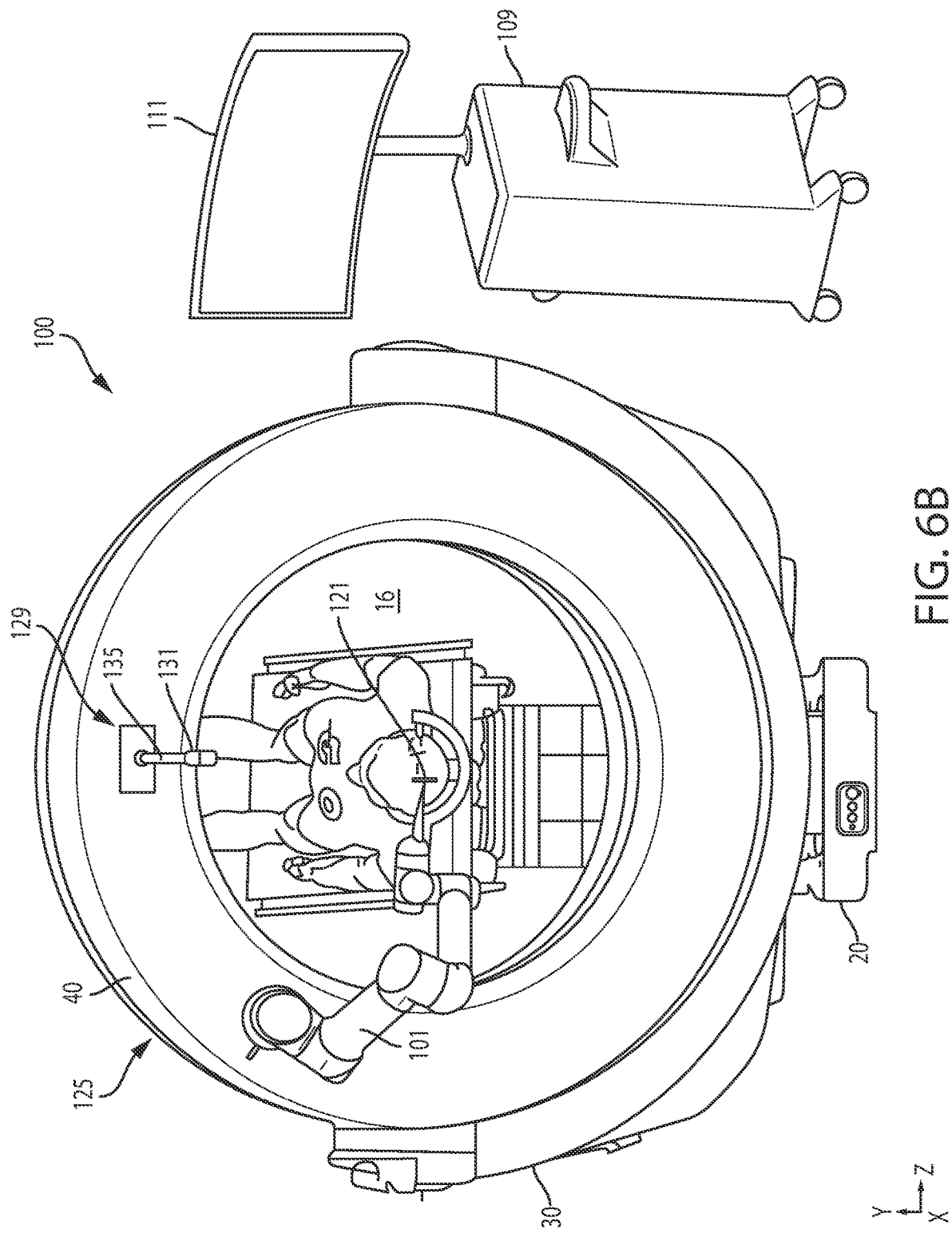
Figure 6C:
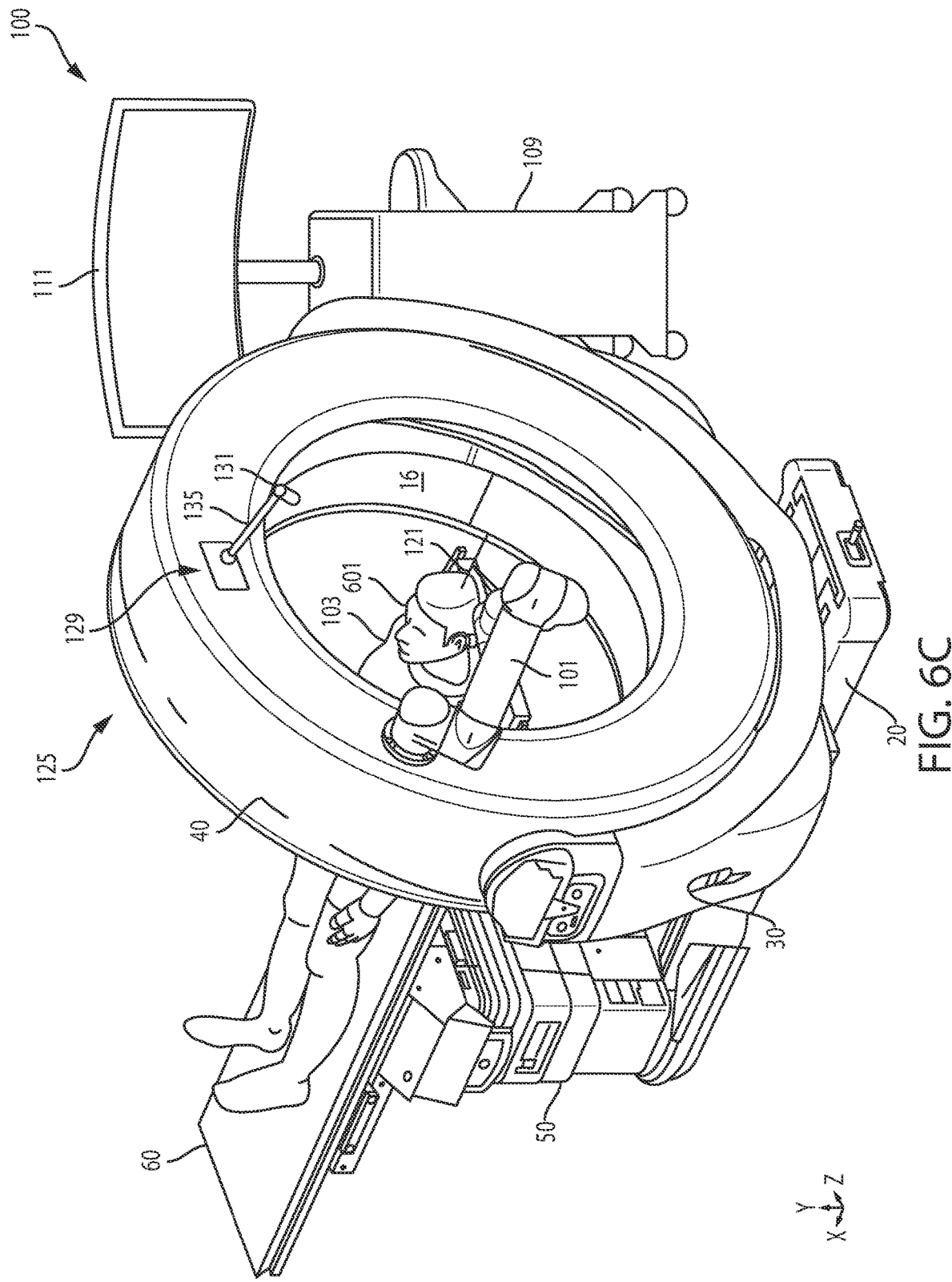

7A-7C show the system of FIGS. 6A-6C with the gantry translated partially along the length of the patient.

FIGS. 8A-8D illustrate a system for performing robotically-assisted surgery including a pair of robotic arms attached to a patient support with a gantry of an imaging system translated to the surgical area of the patient.

Figure 8A:
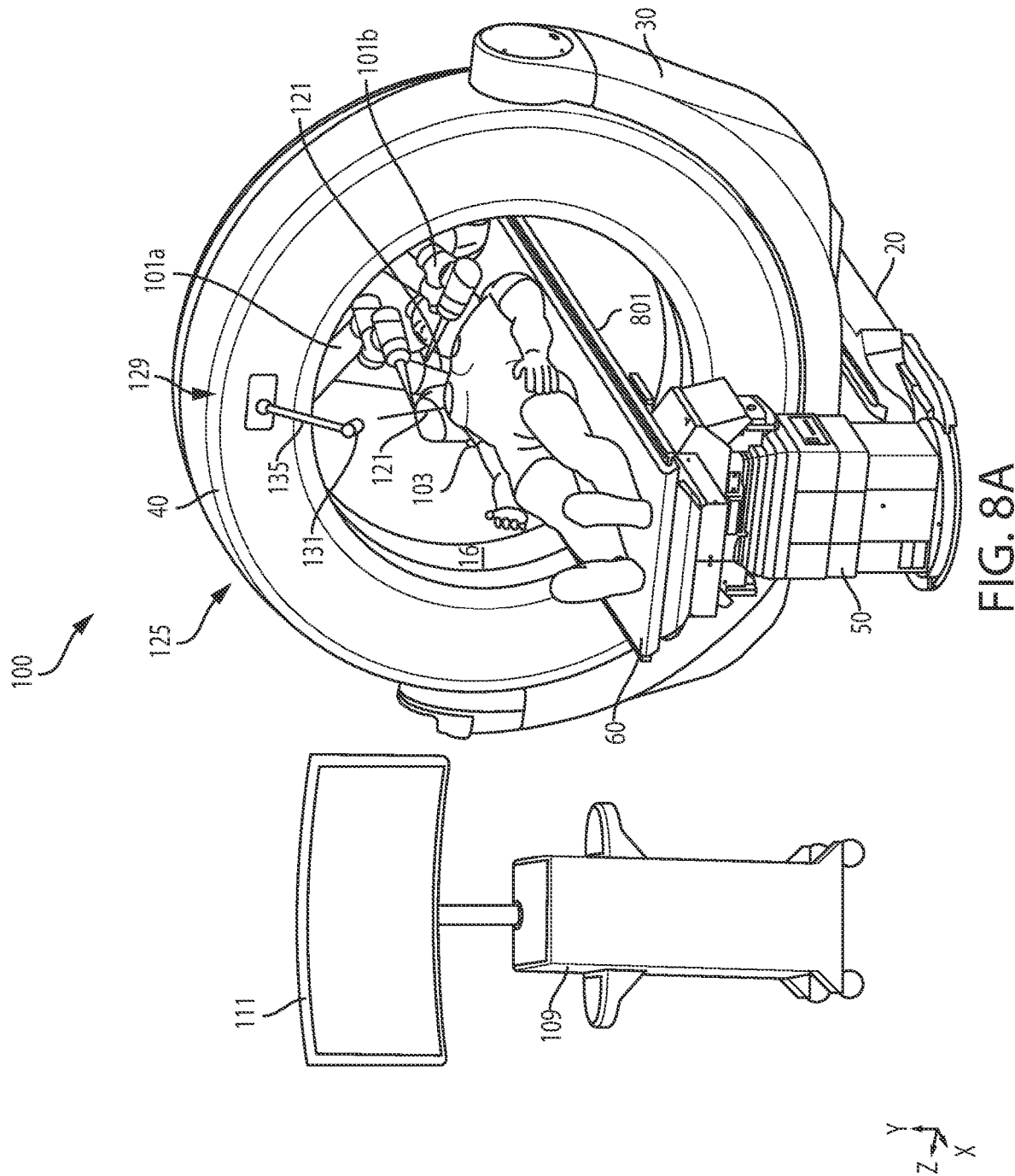
Figure 8B:
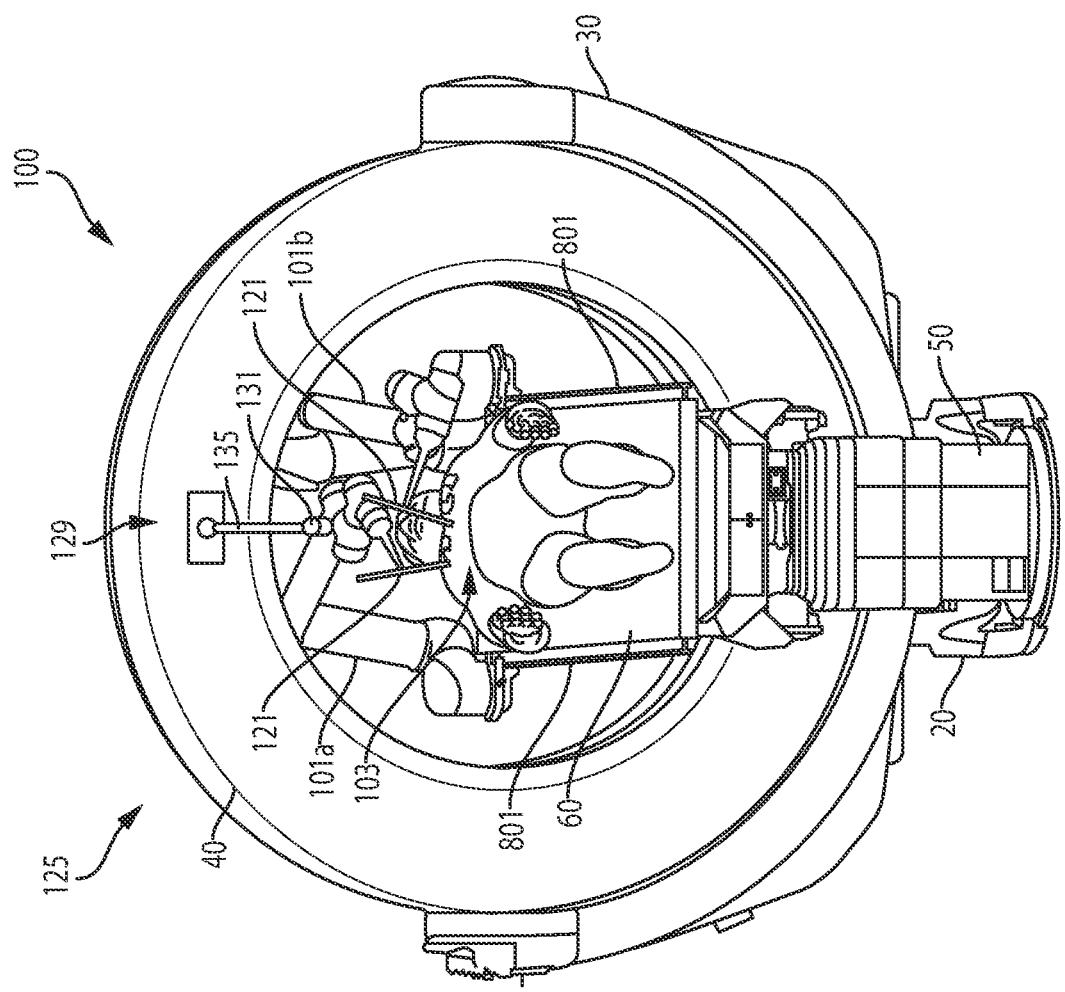
Figure 8B:
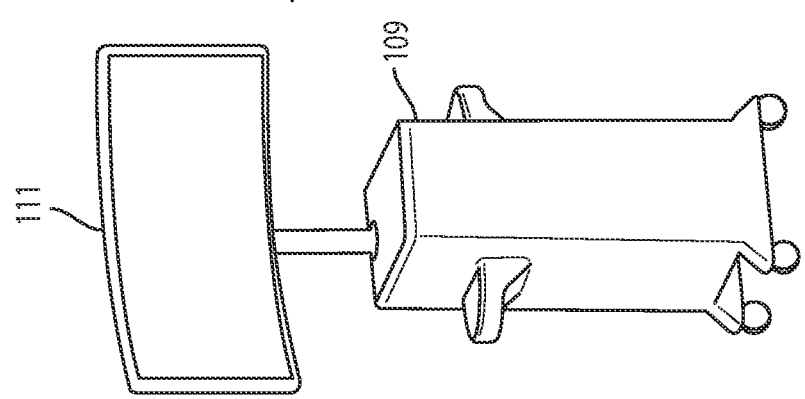
Figure 8C:
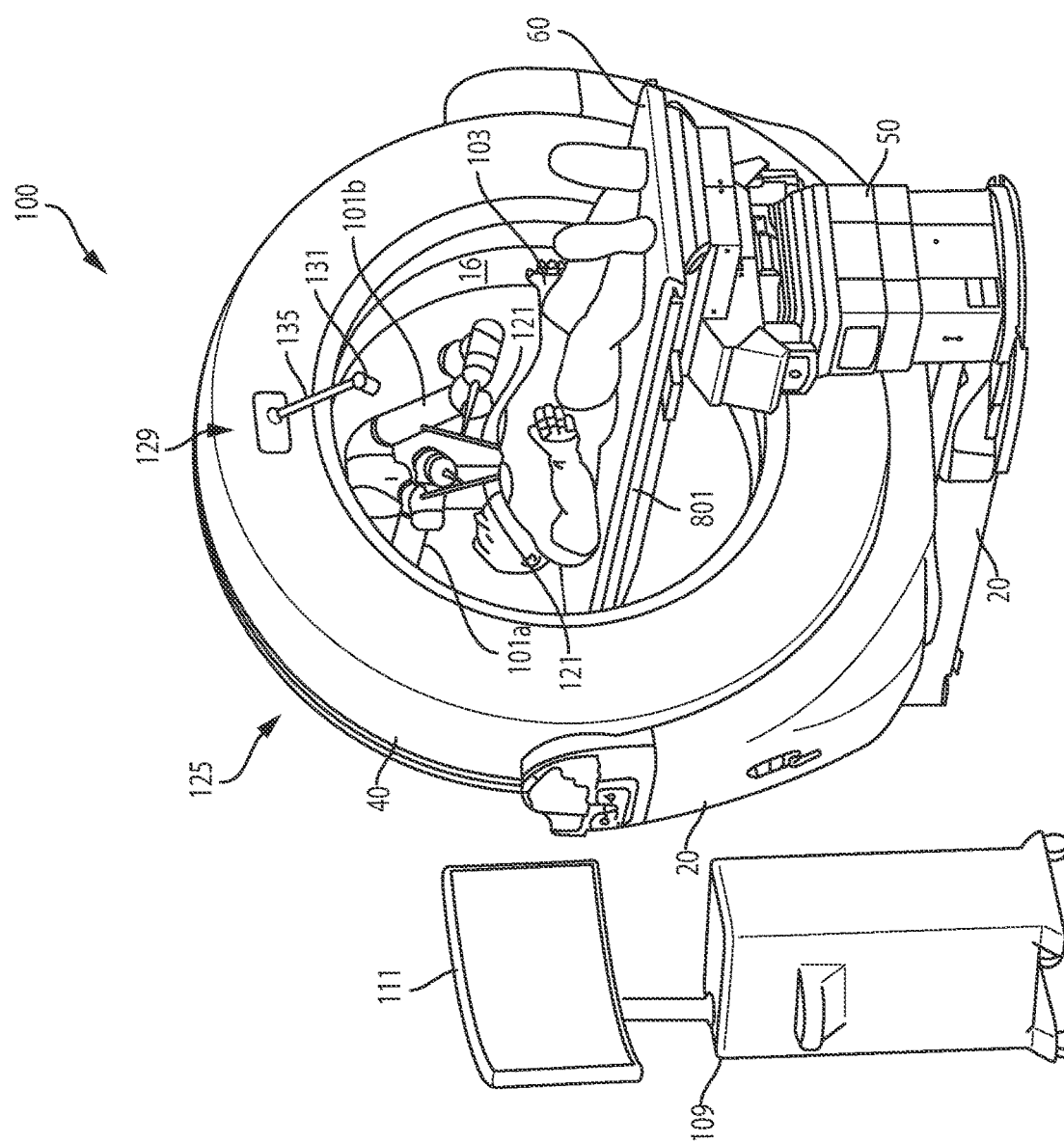
Figure 8D:
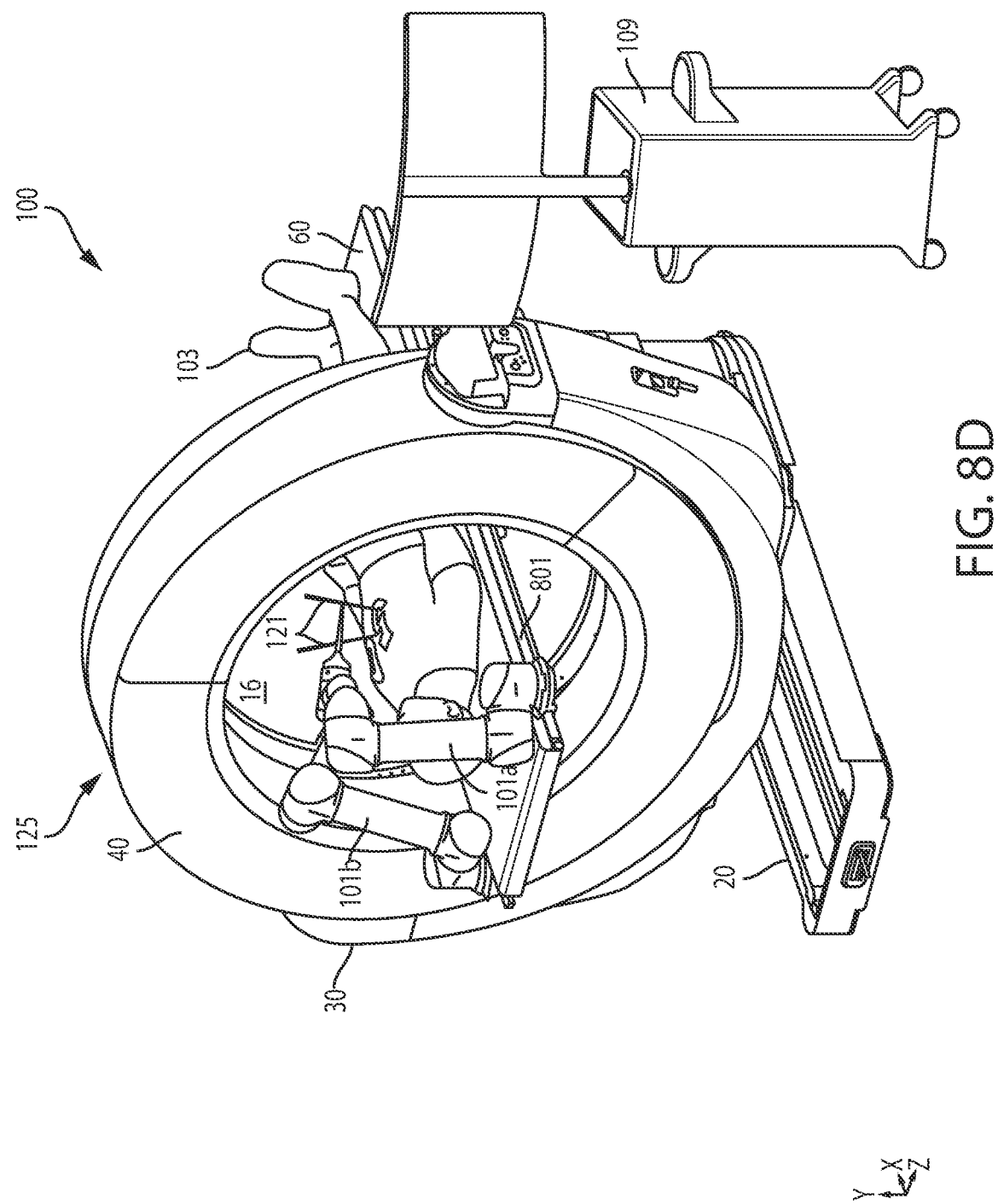
Figure 9A:
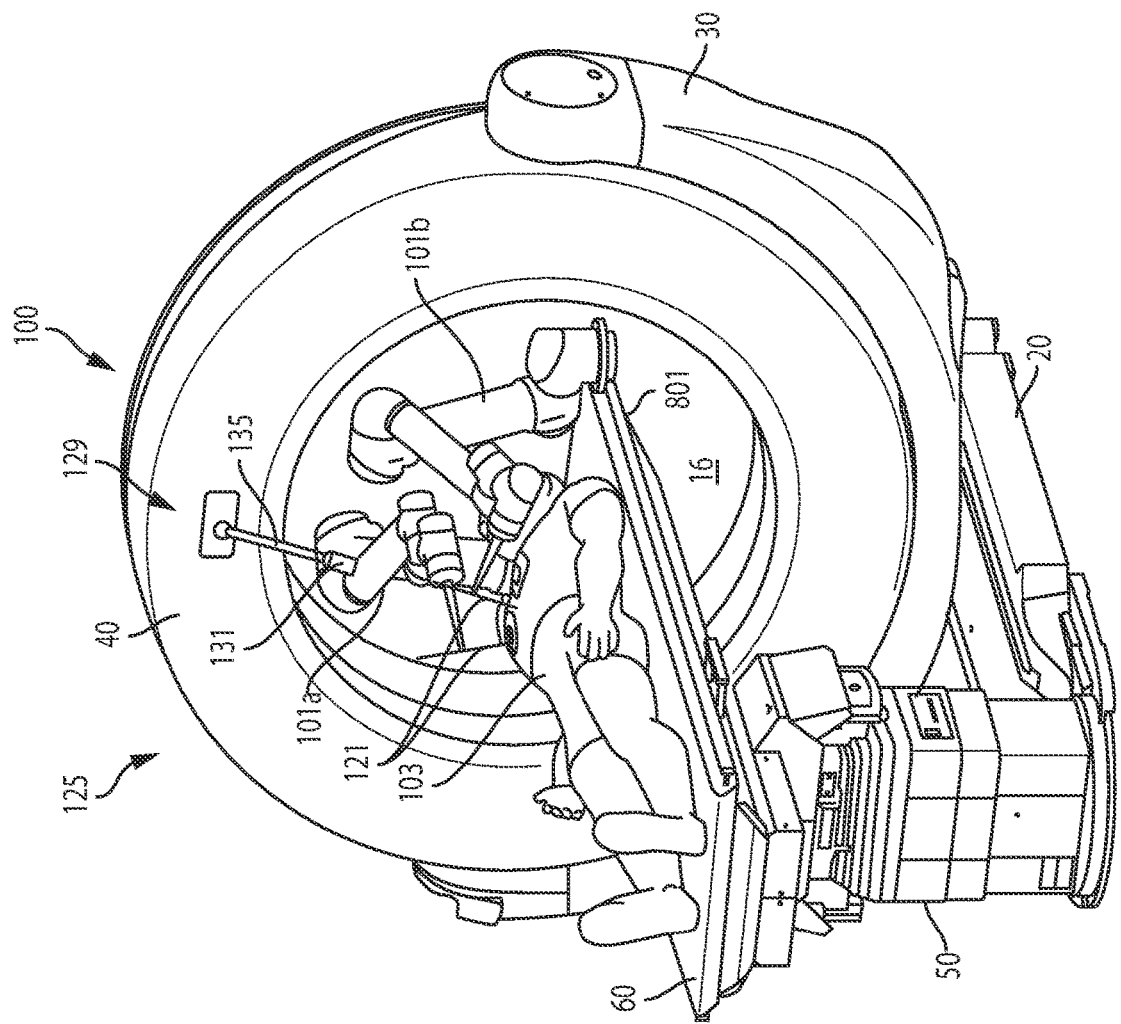
Figure 9A:
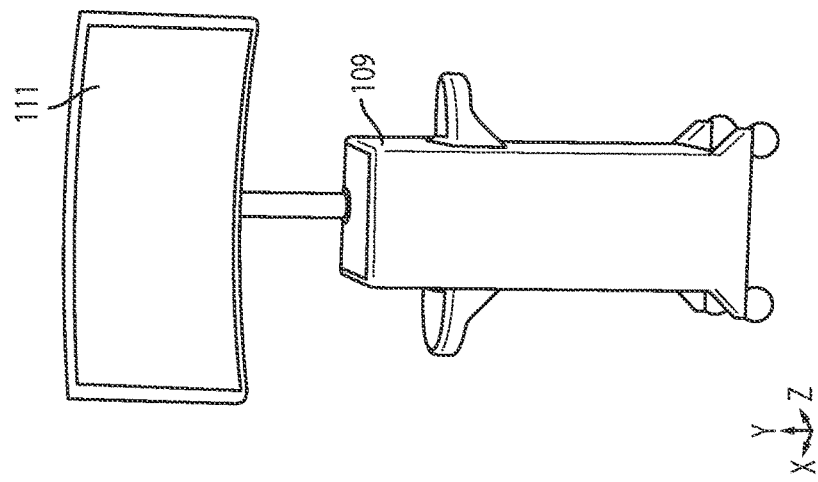
Figure 9B:
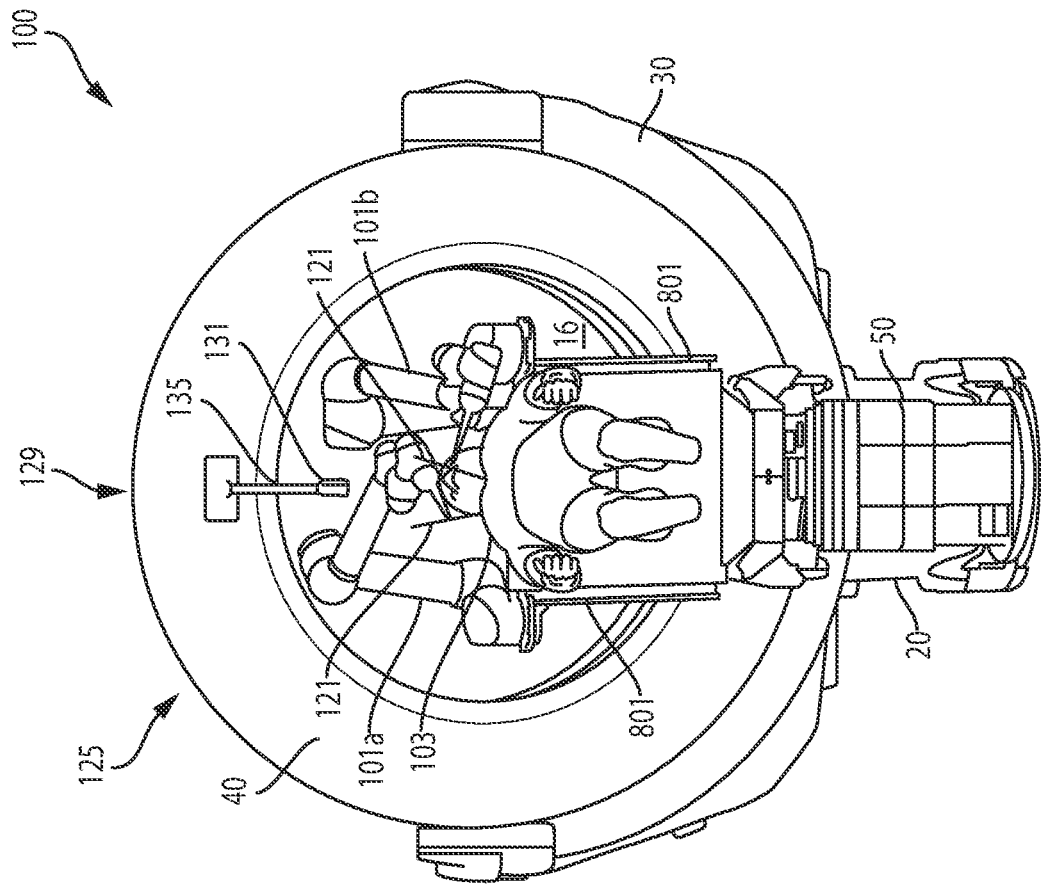
Figure 9B:
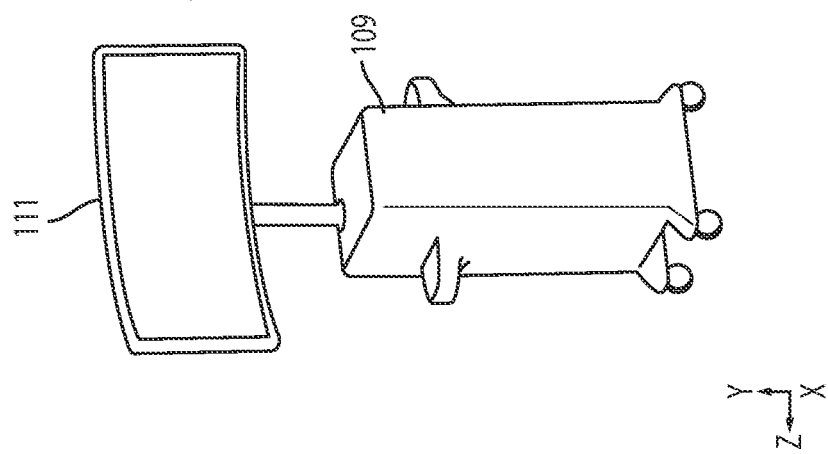

FIGS. 9A-9B illustrate the system of FIGS. 8A-8B with the gantry translated away from the surgical area.

Figure 10A:
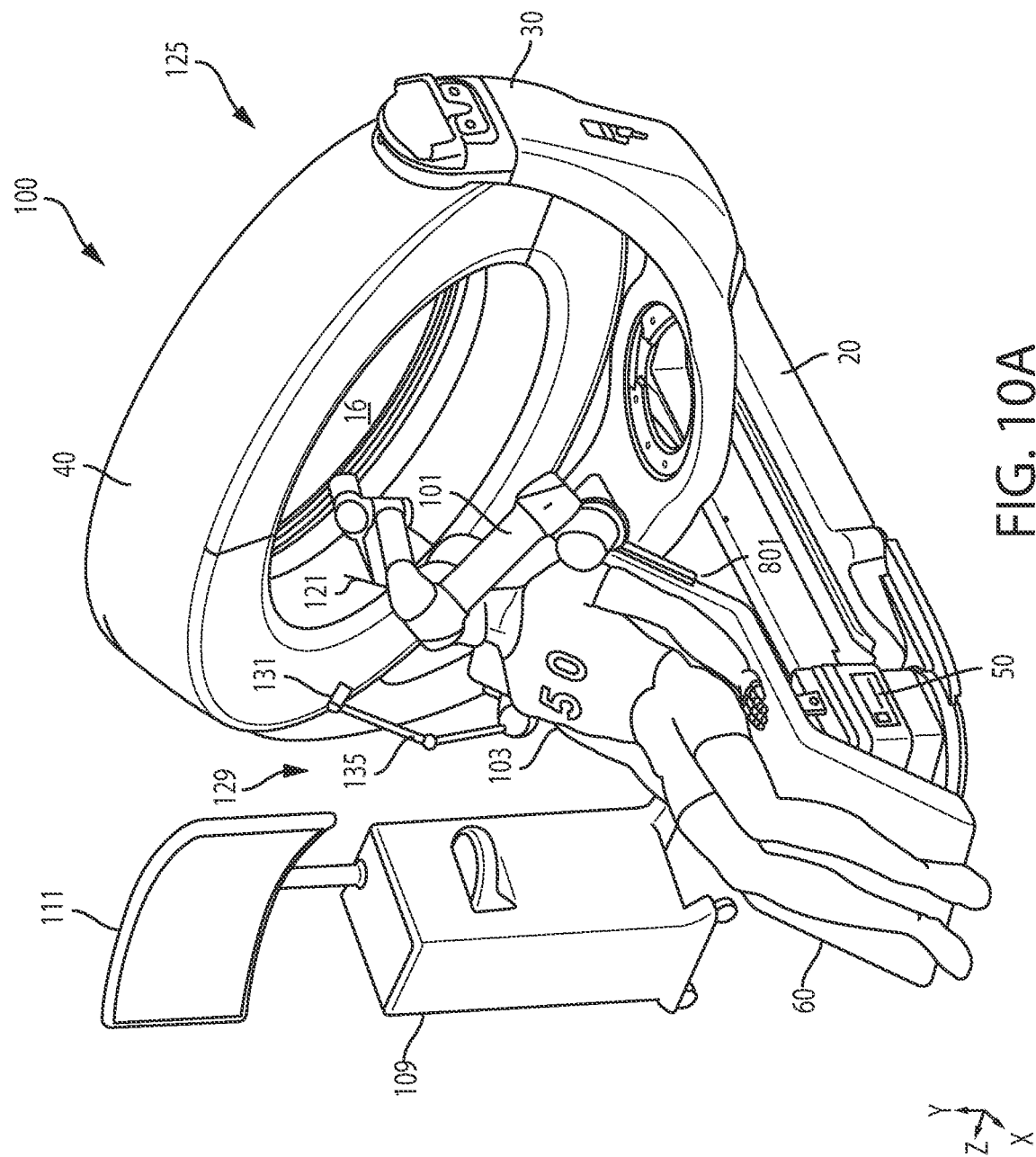
Figure 10B:
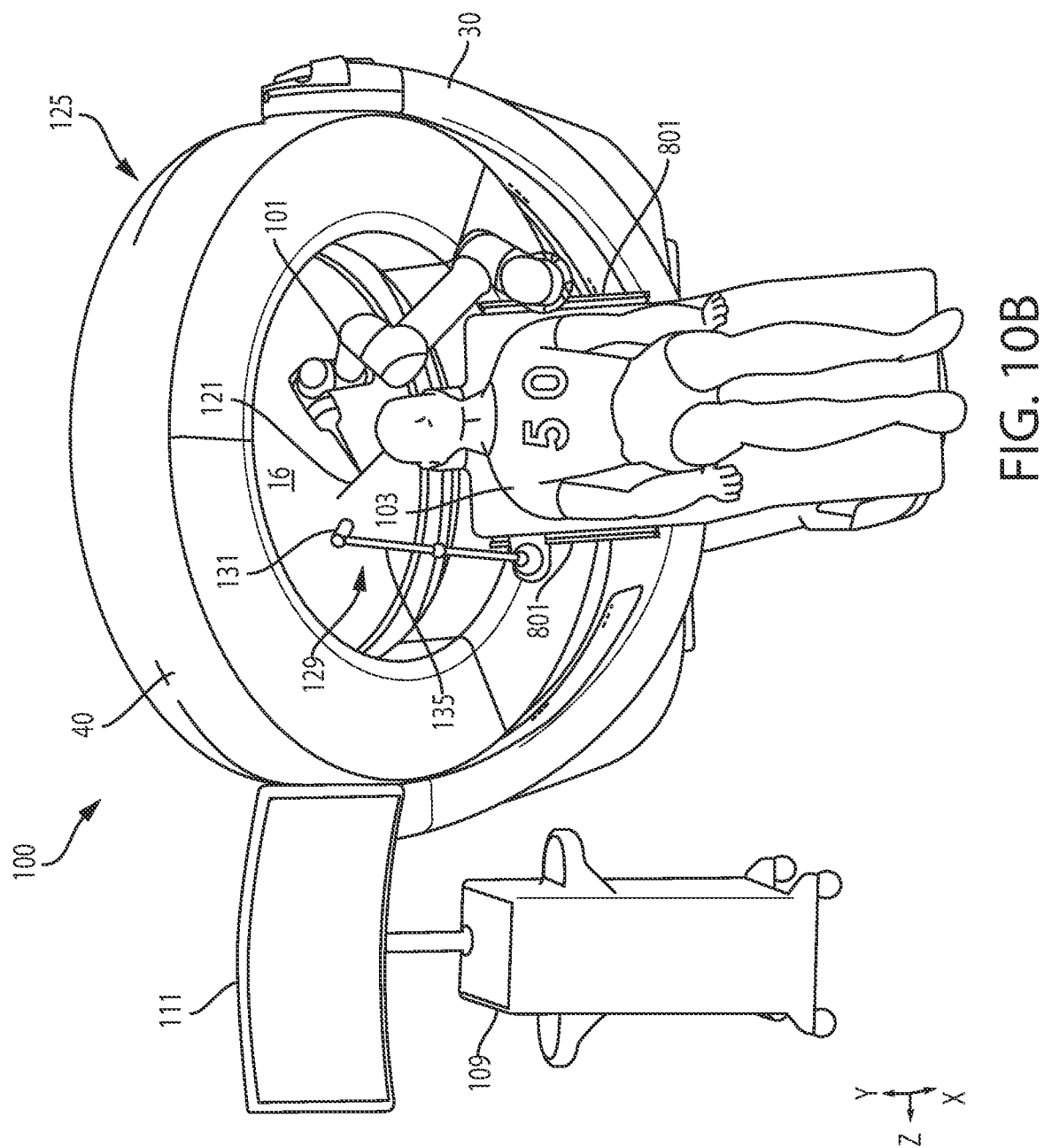
Figure 10C:
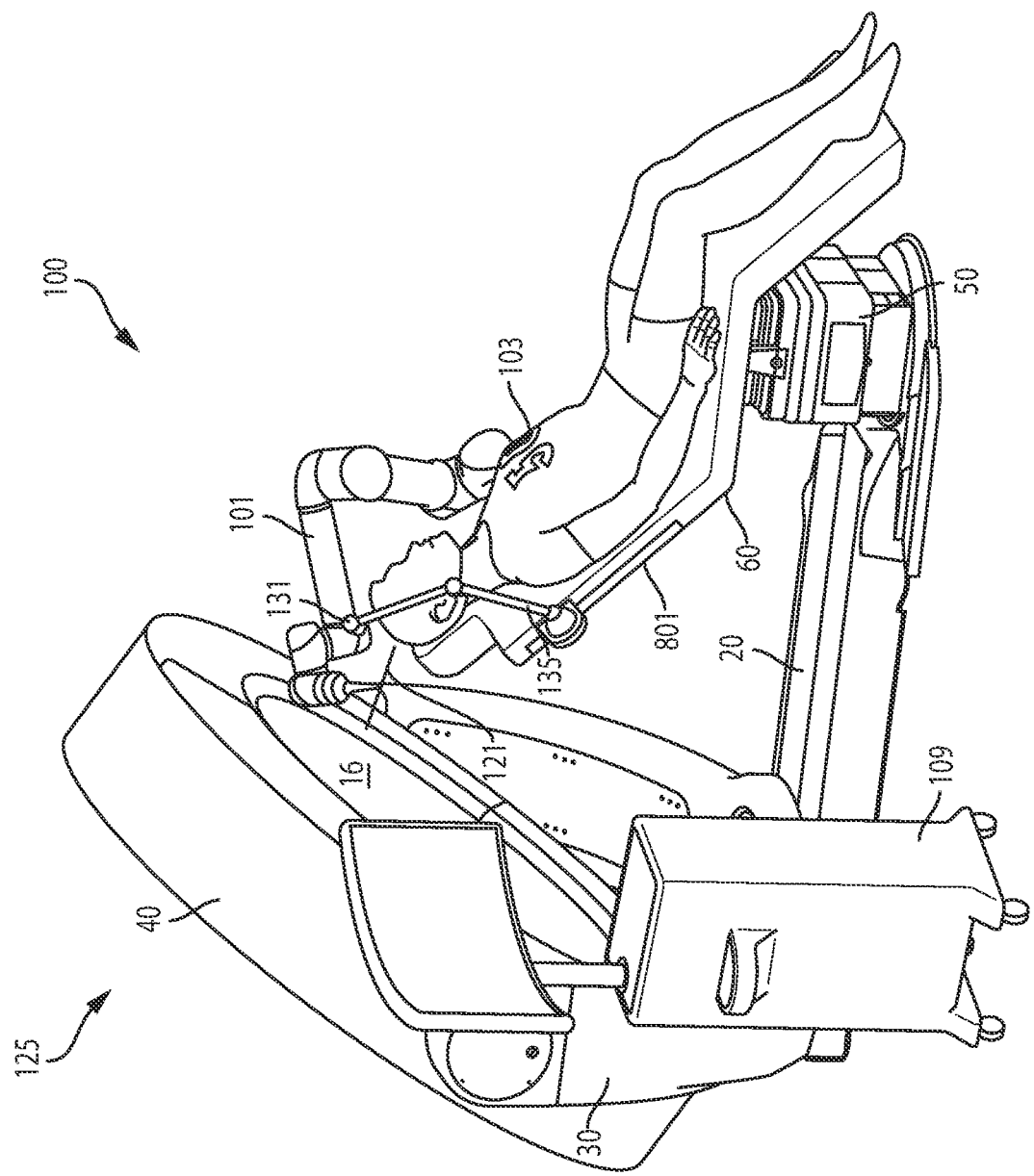

FIGS. 10A-10C illustrate a system for performing robotically-assisted surgery including a robotic arm and a camera for a motion tracking apparatus attached to a patient support for a patient in a sitting position.

Figure 11A:
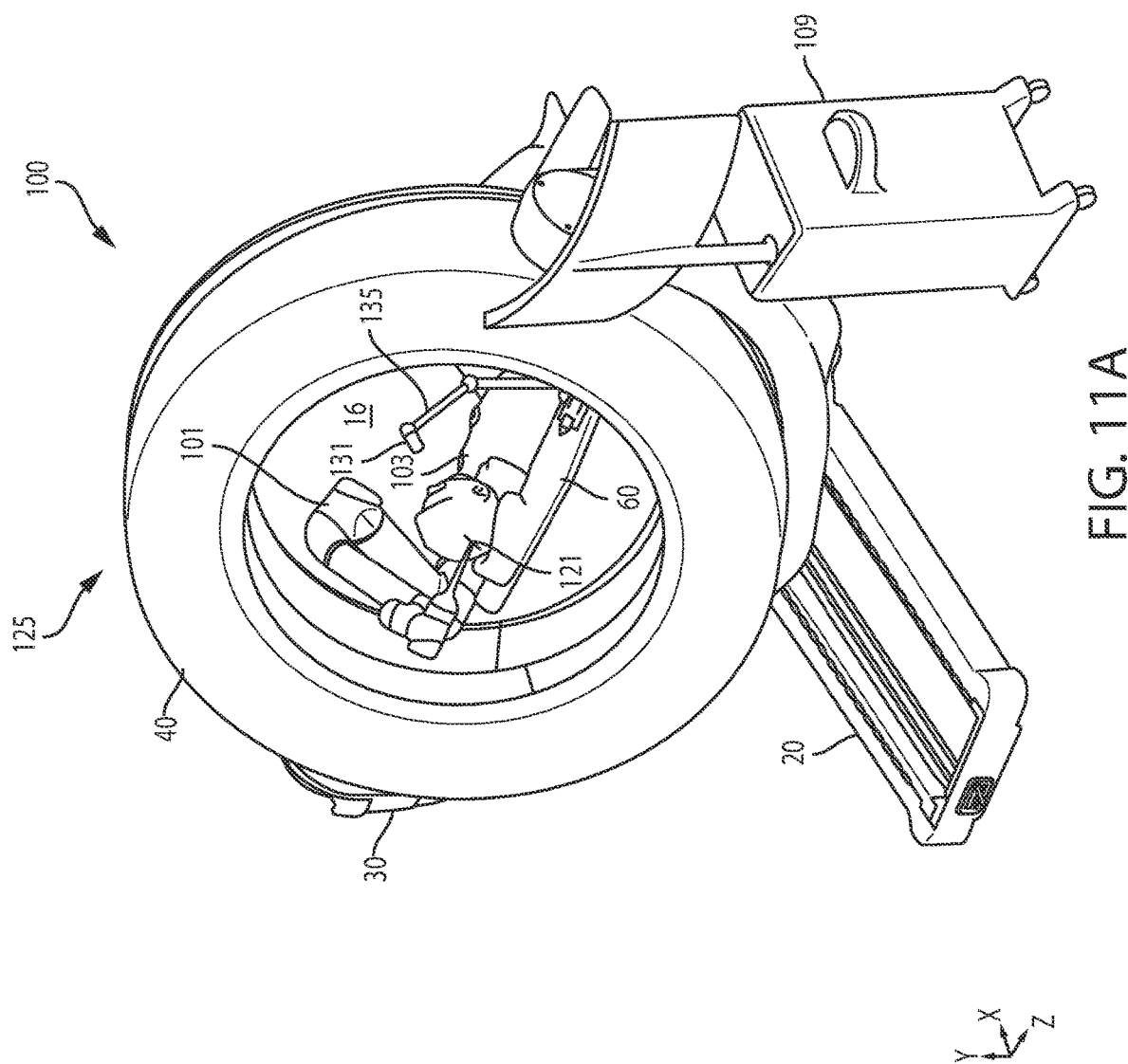
Figure 11B:
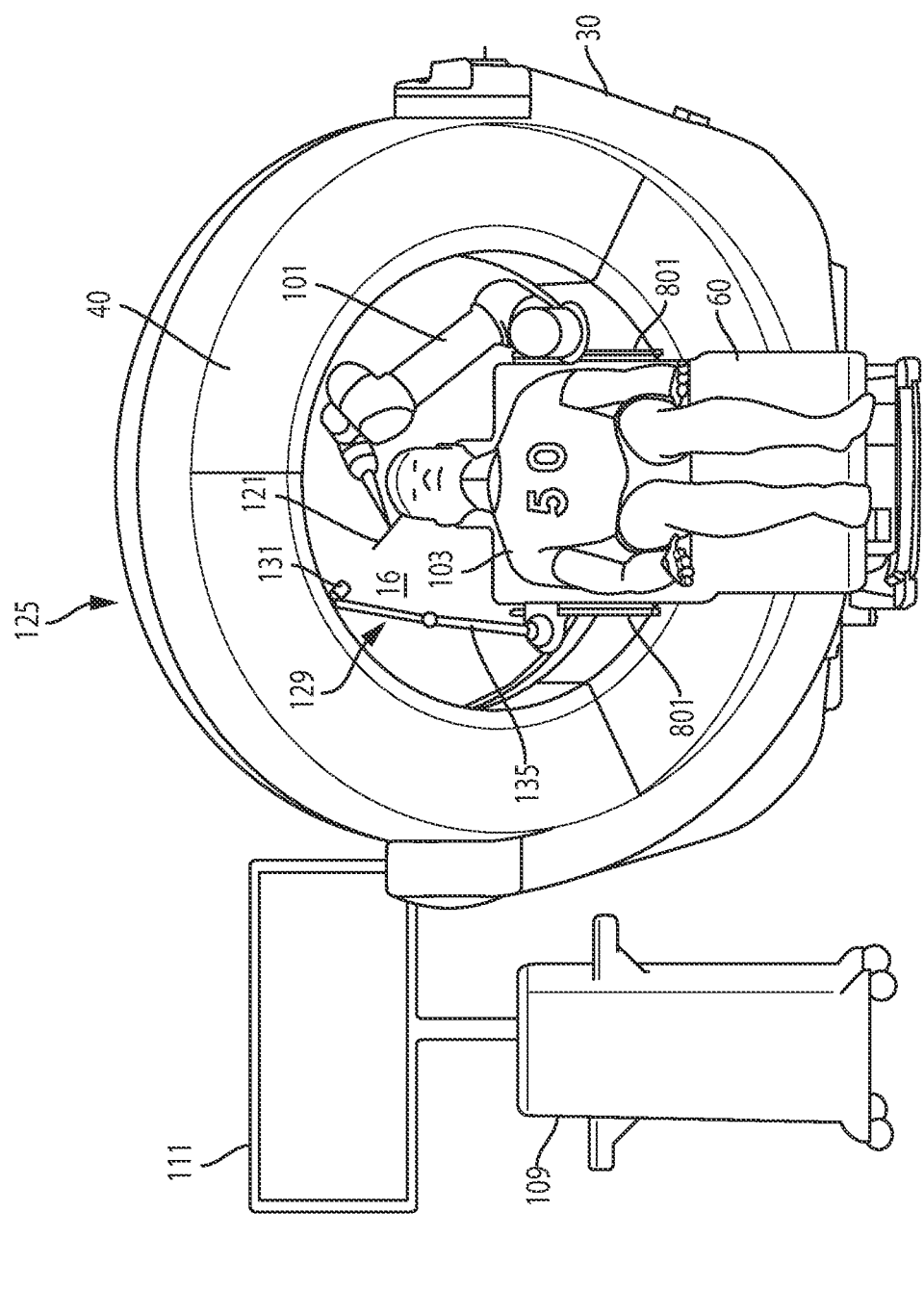
Figure 11C:
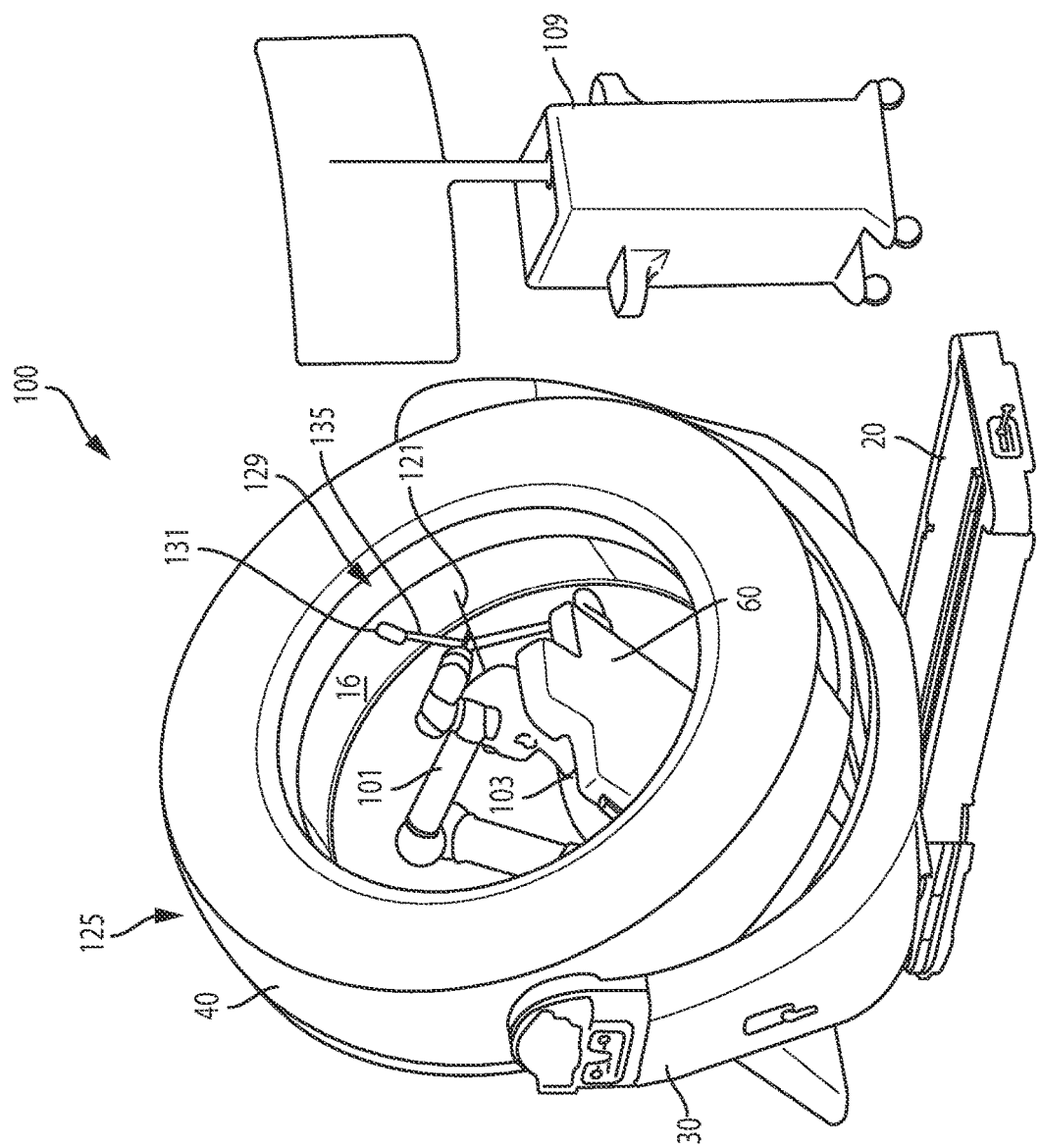

FIGS. 11A-11C illustrate the system of FIGS. 10A-10C with a gantry of an imaging device translated to the surgical area of the patient.

Figure 12A:
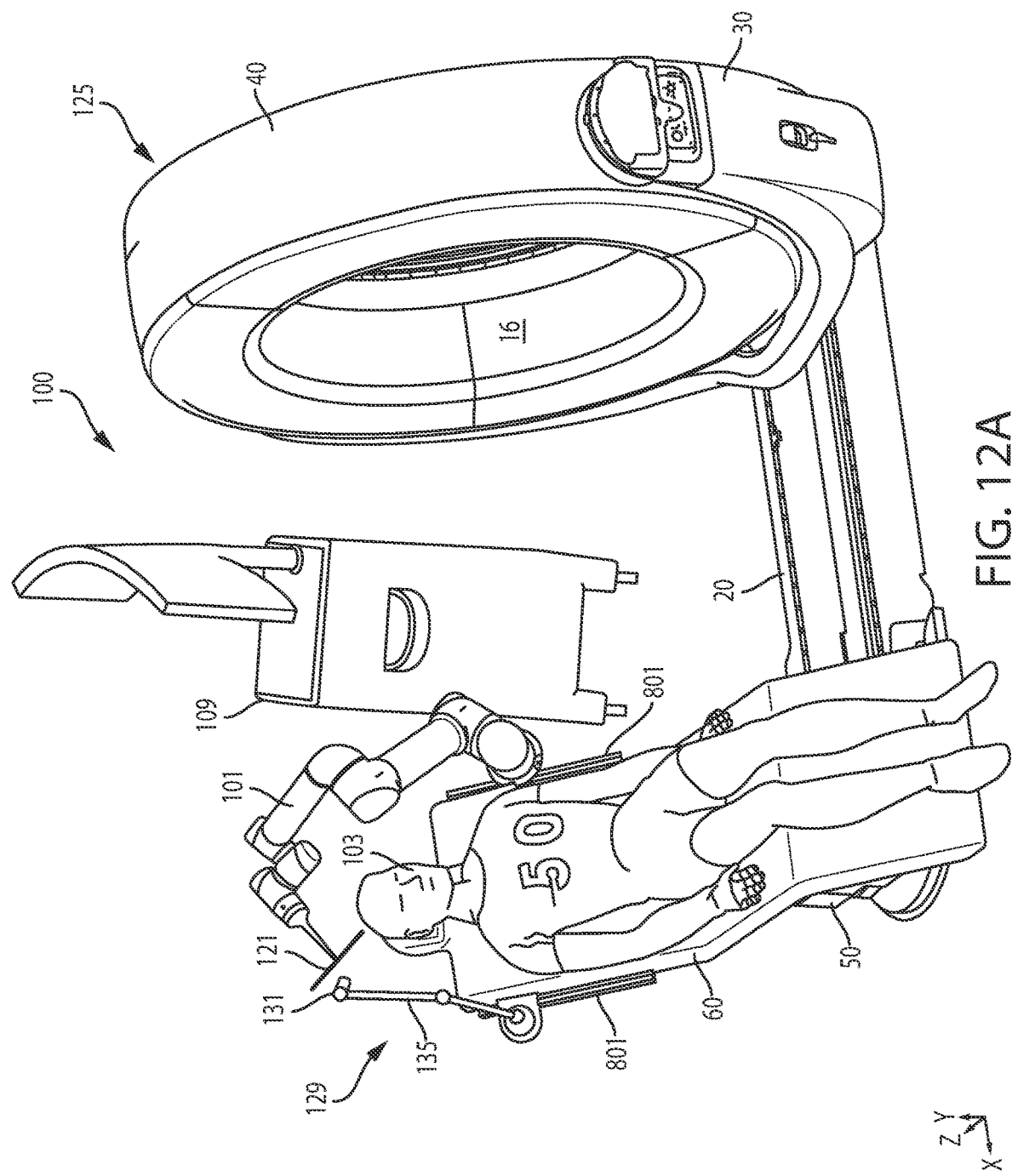
Figure 12B:
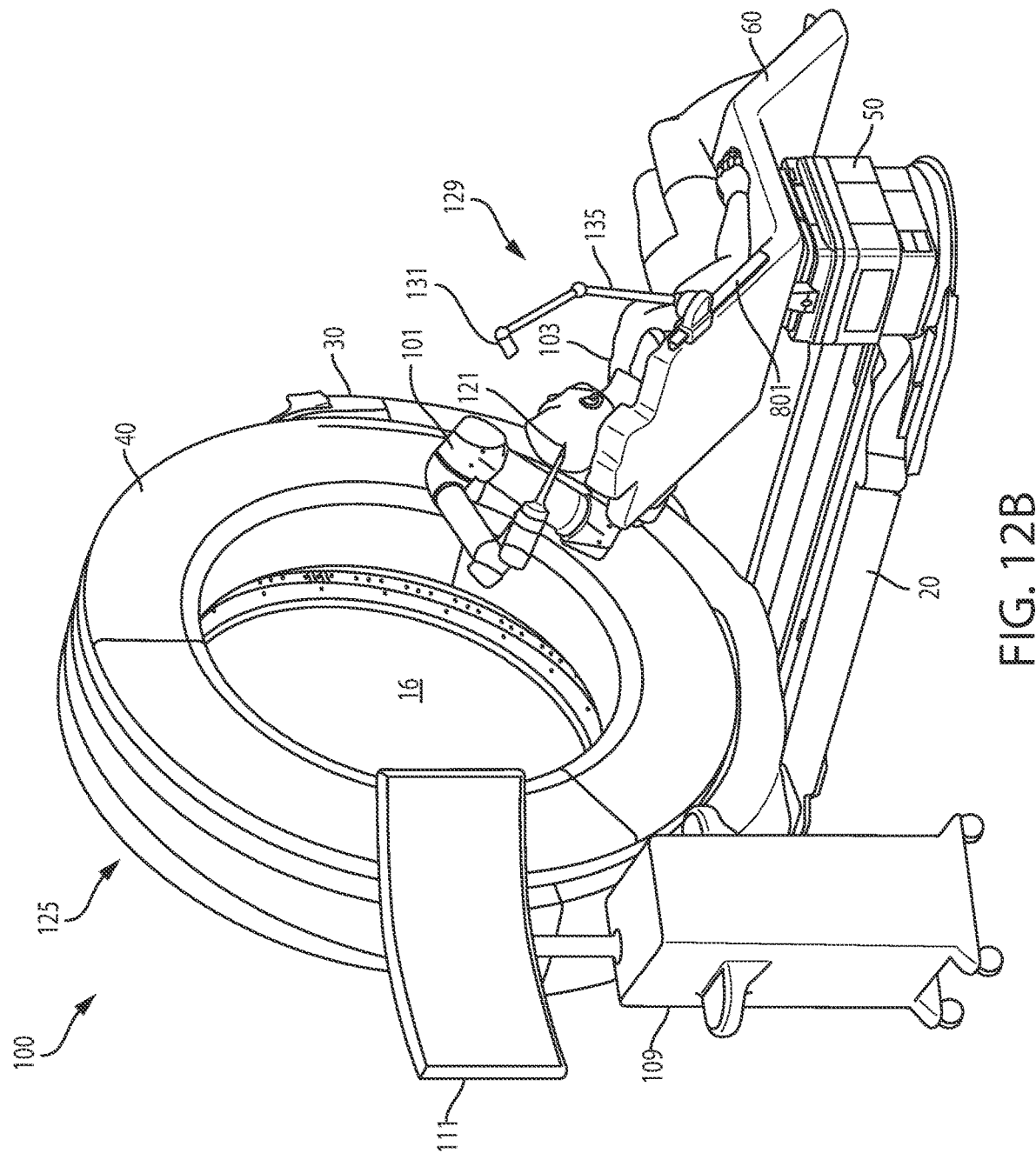

FIGS. 12A-12B illustrate the system of FIGS. 10A-10C and 11A-11C with the patient support rotated with respect to the imaging device.

FIGS. 13A-13D illustrate a system for performing robotically-assisted surgery including a robotic arm attached to a gimbal of an imaging system via a support member.

Figure 14A:
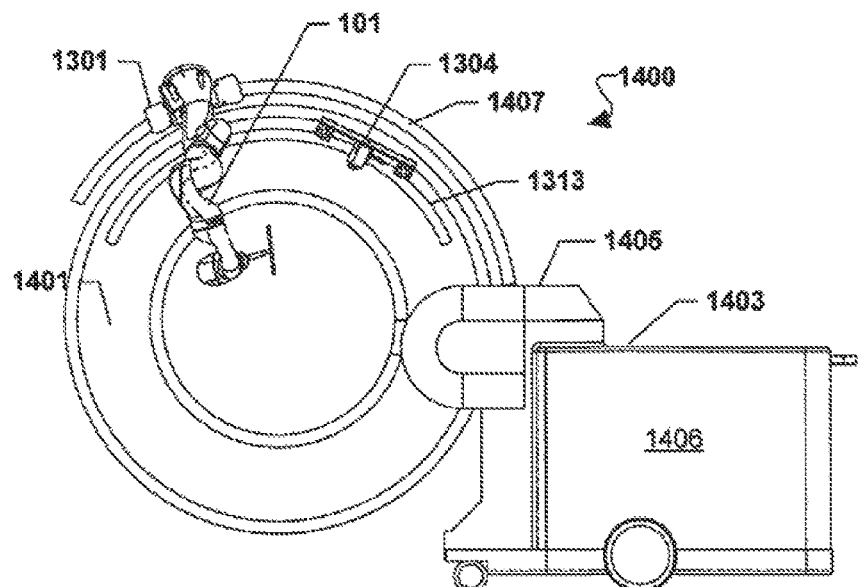
Figure 14B:
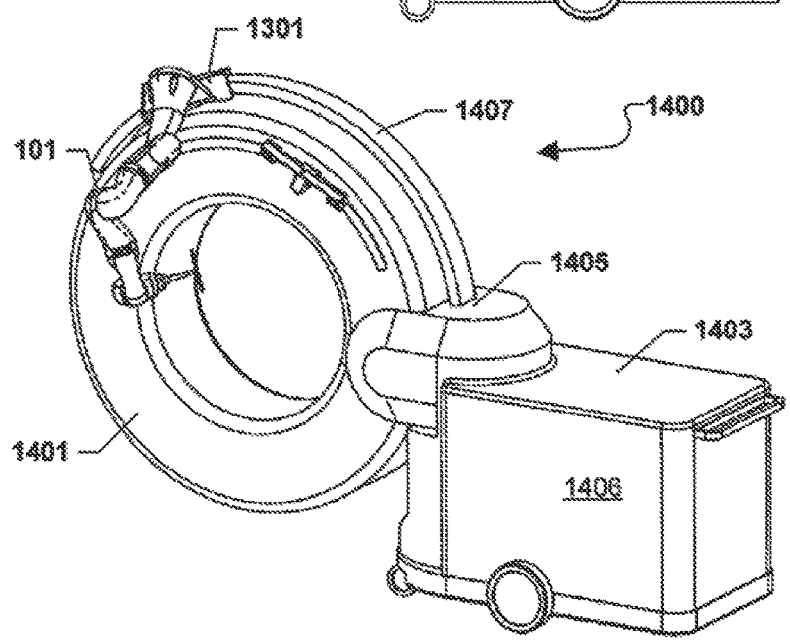
Figure 14C:
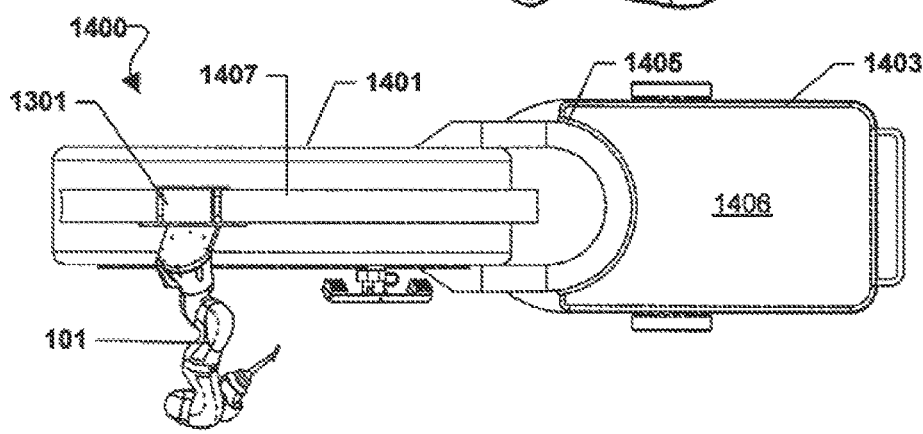

FIGS. 14A-14C are side, perspective and overhead views illustrating a system for performing robotically-assisted surgery including a robotic arm attached to an imaging system having a cantilevered O-shaped imaging gantry.

FIGS. 15A-15D are side, front perspective, rear perspective and overhead views illustrating a system for performing robotically-assisted surgery including a robotic arm attached to a C-arm imaging system.

Figure 16:
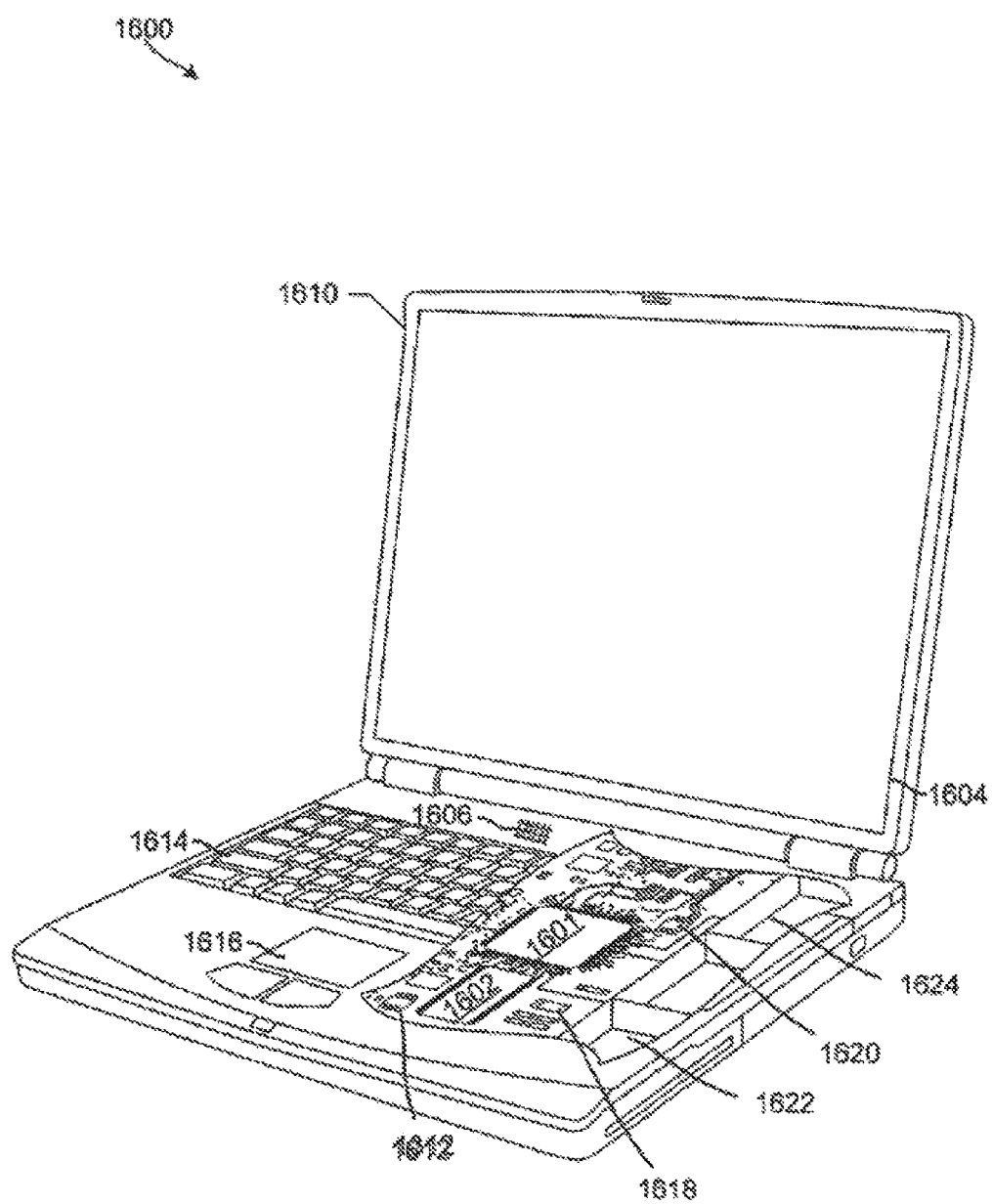

FIG. 16 schematically illustrate a computing device which may be used for performing various embodiments.

DETAILED DESCRIPTION

The various embodiments will be described in detail with reference to the accompanying drawings. Wherever possible, the same reference numbers will be used throughout the drawings to refer to the same or like parts. References made to particular examples and implementations are for illustrative purposes, and are not intended to limit the scope of the invention or the claims.

Various embodiments are directed to an integrated system for performing robotically-assisted surgery in conjunction with intra-operative imaging. In recent years, there has been increased interest in the field of robotically-assisted surgery in which robotic systems are used to aid in surgical procedures. However, such systems are generally characterized by high-cost and complexity and may also be limited in the types of procedures they can perform. Various embodiments include systems and methods for performing robotically-assisted surgery that may be characterized by improved usability, workflow and ease of use. The systems and methods of various embodiments may be used to perform a wide variety of surgical procedures in virtually any part of a patient's anatomy.

Figure 1A:
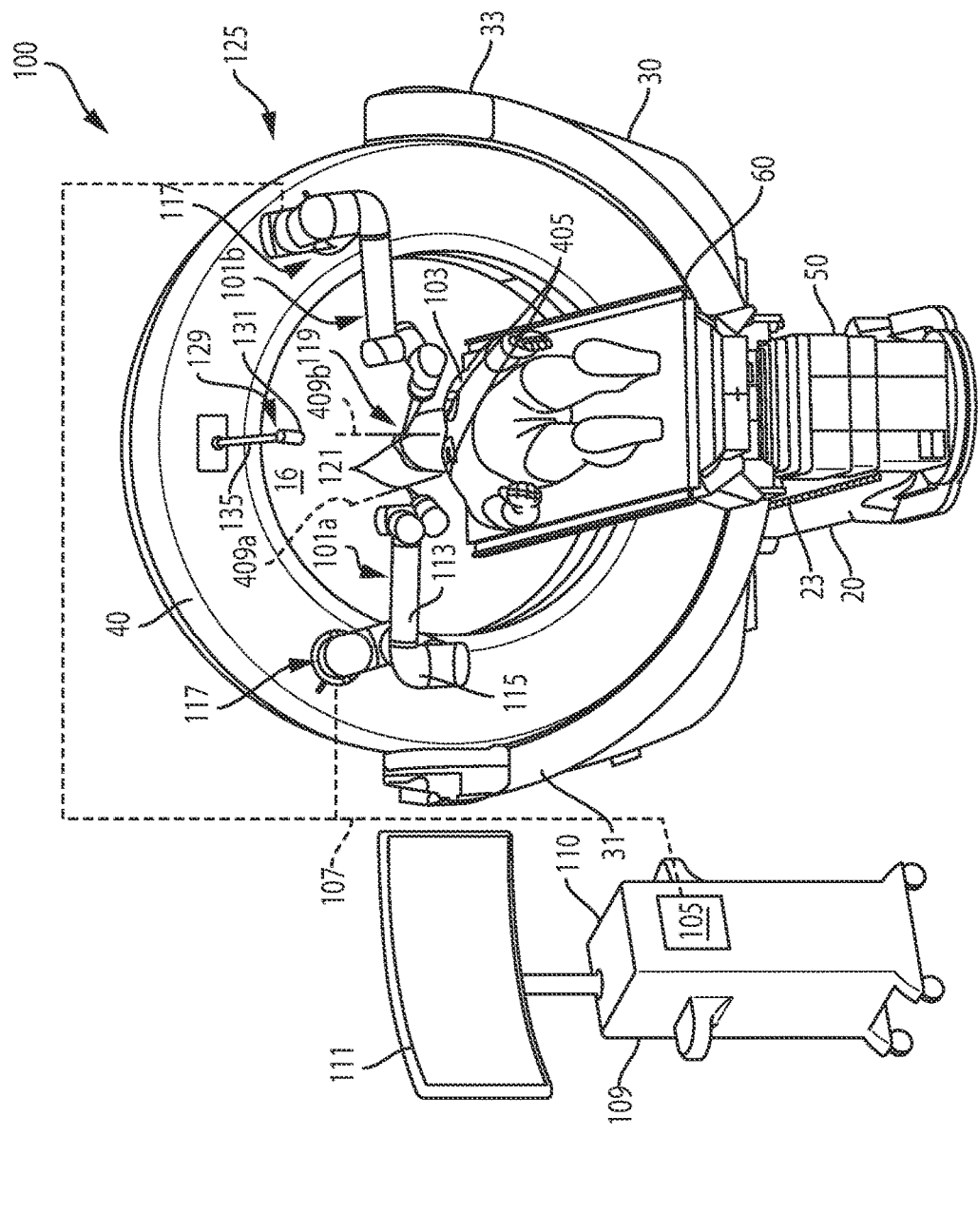
FIGS. 1A-1C are perspective views showing the front (FIGS. 1A and 1C) and rear (FIG. 1B) sides of a system for performing robotically-assisted surgery including a pair of robotic arms attached to a gantry of an imaging device according to one embodiment.
Figure 1B:
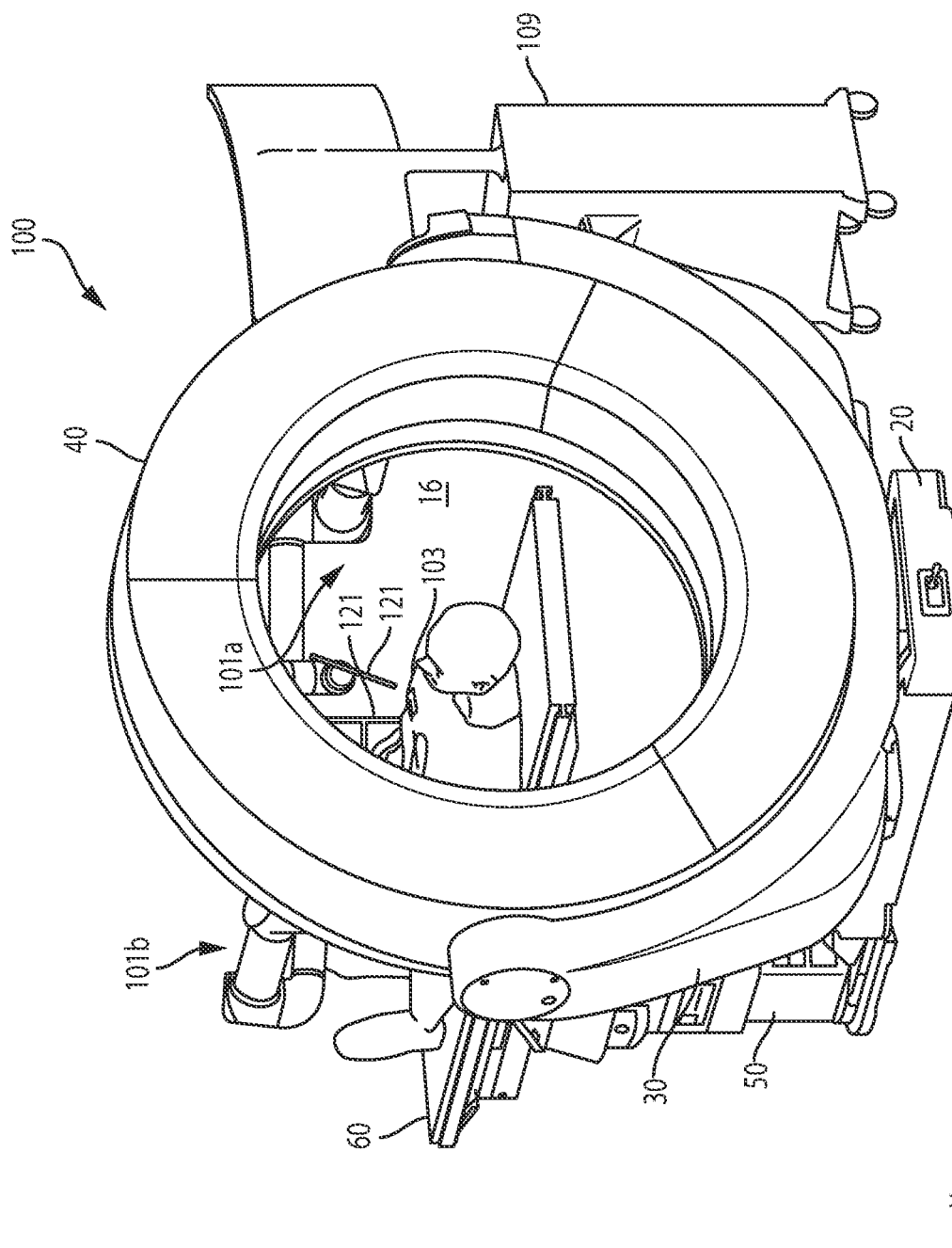
Figure 1C:
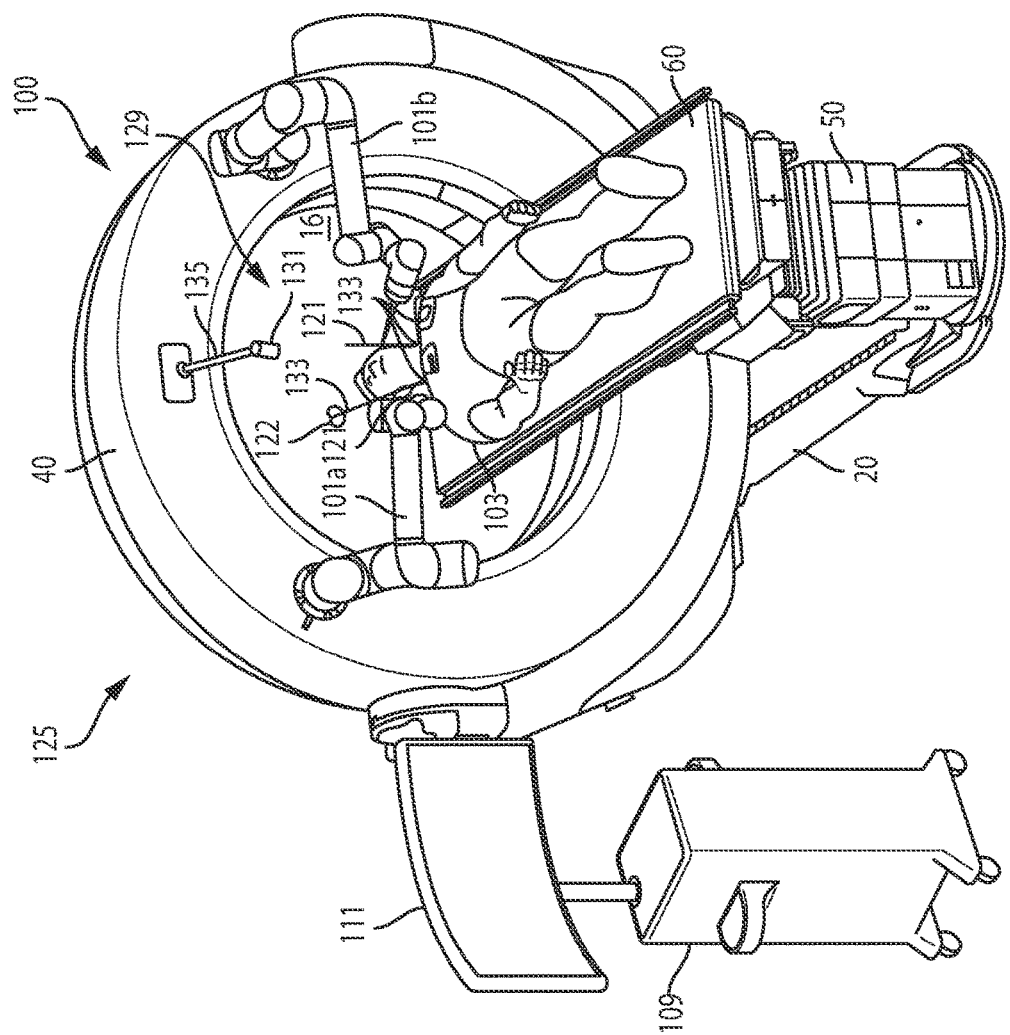

A system 100 for performing robotically-assisted surgery according to one embodiment is shown in FIGS. 1A-1C. FIGS. 1A and 1C are perspective views showing the first (i.e., front) side of the system 100 and FIG. 1B is a perspective view showing a second (i.e., rear) side of the system 100. The system 100 includes at least one robotic arm 101 that is movable with respect to a patient 103. In this embodiment, the system 100 includes two robotic arms 101a, 101b that may be moved independently of one another. It will be understood that in other embodiments, the system 100 may include a single robotic arm or more than two robotic arms. The movements of the robotic arm(s) 101a, 101b may be controlled by a controller 105 (e.g., a computer including a memory and processor for executing software instructions) that may be coupled to the robotic arm(s) 101a, 101b via a wired or wireless link 107. In this embodiment, the controller 105 for the robotic arms 101a, 101b is located in a workstation/mobile cart 109 that may include a display 111 and one or more user input devices 100 (e.g., touchscreen controller, keyboard, mouse, buttons, switches, etc.) to enable a user to control the operation of the system 100.

In this embodiment, each of the robotic arms 101a, 101b comprises a multi-joint arm that includes a plurality of linkages 113 connected by joints 115 having actuator(s) and optional encoder(s) to enable the linkages to bend, rotate and/or translate relative to one another in response to control signals from the control system 105. A first end 117 of the robotic arm 101a, 101b may be fixed to a structure 40 and a second end 119 of the arm may be freely movable with respect to the first end 117. An end effector 121 is attached to the second end 119 of the robotic arm 101a, 101b. In some embodiments, the end effector 121 may be an invasive surgical tool, such as a needle, a cannula, a cutting or gripping instrument, an endoscope, etc., that may be inserted into the body of the patient. In other embodiments, as described in further detail below, the end effector 121 of the robotic arm 101a, 101b may be a hollow tube or cannula that may receive an invasive surgical tool 122 (see FIG. 1C), including without limitation a needle, a cannula, a tool for gripping or cutting, an electrode, an implant, a radiation source, a drug and an endoscope. The invasive surgical tool 122 may be inserted into the patient's body through the hollow tube or cannula by a surgeon. An end effector 121 comprising a hollow tube or cannula may be made of a radiolucent material, such as a carbon-fiber or thermoplastic material.

The patient 103, which may be a human or animal patient, may be located on a suitable patient support 60, which may be a surgical table as shown in FIGS. 1A-1C. The patient support 60 in this embodiment is raised off the ground by a support column 50. During a surgical procedure, the robotic arms 101a, 101b may be located partially or completely within the sterile surgical field, and thus may be covered by a surgical drape or other sterile barrier (not shown for clarity). In embodiments, the end effector 121 (e.g., a hollow tube or cannula) may be a sterilized component that may be attached (e.g., snapped into) the end 119 of the robotic arm 101 over the drape. The end effector 121 may be a sterile, single-use (i.e., disposable) component that may be removed and discarded after use.

The system 100 also includes an imaging device 125 that may be used to obtain diagnostic images of the patient 103. The imaging device 125 may be located in proximity to both the patient 103 and the at least one robotic arm 101a, 101b (e.g., within 10 meters, such as less than 5 meters, including 0-3 meters from the patient 103 and arm(s) 101a, 101b), and is preferably located within the same room (e.g., an operating room). In the embodiment of FIGS. 1A-1C, the imaging device 125 includes a base 20 and a gantry 40 located above the base 20. The gantry 40 in this embodiment includes a substantially O-shaped housing (i.e., a ring) defining a bore 16. The gantry 40 includes one or more imaging components (not shown for clarity) located within the housing of the gantry 40 that are configured to obtain image data of at least a portion of an object (e.g., patient 103) positioned within the bore 16. In this embodiment, the first end 117 of each of the robotic arms 101a, 101b is attached to the imaging device 125. In particular, each of the robotic arms 101a, 101b are attached to a first (i.e., front) side 127 of the gantry 40, although it will be understood that the robotic arms 101a, 101b may be mounted at other portions of the imaging device 125 or system 100. In embodiments, the imaging device 125 may include one or more adaptors configured to receive a robotic arm 101 at one or more locations on the device 125. The adaptor(s) may be molded or affixed (e.g., using fasteners or adhesive) to an outer surface of the device 125. The first end 117 of a robotic arm 101 may be inserted into and secured by the adaptor. After use, the robotic arm(s) 101 may be released from the adaptor and removed from the imaging device 125 for transport and/or storage. For example, the robotic arms 101a, 101b may be stored on and/or transported by the cart 109.

In embodiments, the imaging device 125 may be an x-ray computed tomography (CT) imaging device. The imaging components within the gantry 40 may include an x-ray source and an x-ray detector. The x-ray source and optionally the detector may rotate within the gantry 40 around the bore 16 to obtain x-ray image data (e.g., raw x-ray projection data) of an object located within the bore 16. The collected image data may be processed using a suitable processor (e.g., computer) to perform a three-dimensional reconstruction of the object, which may be, for example, rendered on the display 111. Examples of x-ray CT imaging devices that may be used according to various embodiments are described in, for example, U.S. Pat. No. 8,118,488, U.S. Patent Application Publication No. 2014/0139215, U.S. Patent Application Publication No. 2014/0003572, U.S. Patent Application Publication No. 2014/0265182 and U.S. Patent Application Publication No. 2014/0275953, the entire contents of all of which are incorporated herein by reference. It will be understood that these embodiments are provided as illustrative, non-limiting examples of imaging systems suitable for use in the present systems and methods, and that the present systems and methods may utilize various types of medical imaging devices. For example, alternatively or in addition to an x-ray CT device, the imaging device 125 may be an x-ray fluoroscopic imaging device, a magnetic resonance (MR) imaging device, a positron emission tomography (PET) imaging device, a single-photon emission computed tomography (SPECT), an ultrasound imaging device, etc.

Figure 2A:
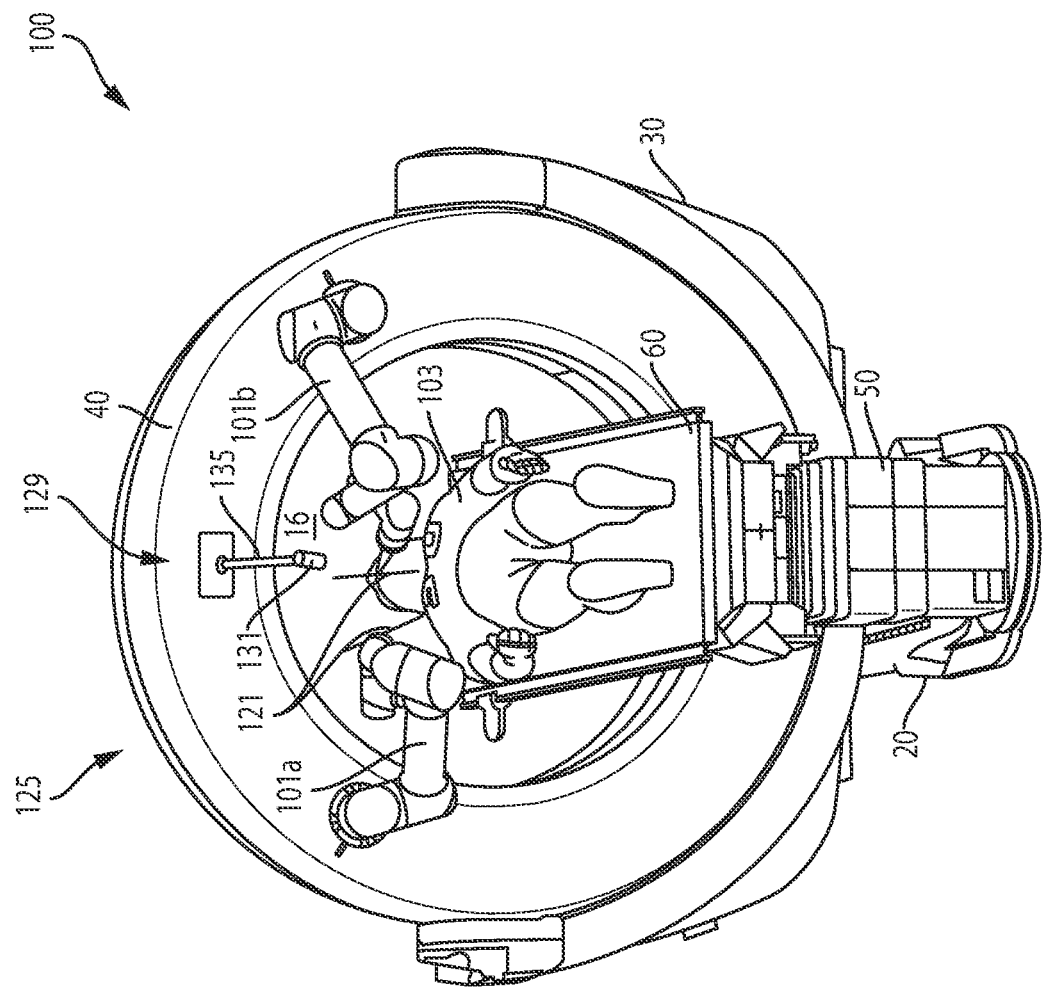
FIGS. 2A-2C are perspective views showing the front (FIGS. 2A and 2C) and rear (FIG. 2B) sides of the system of FIGS. 1A-1C with the gantry translated to the surgical area of the patient.
Figure 2A:
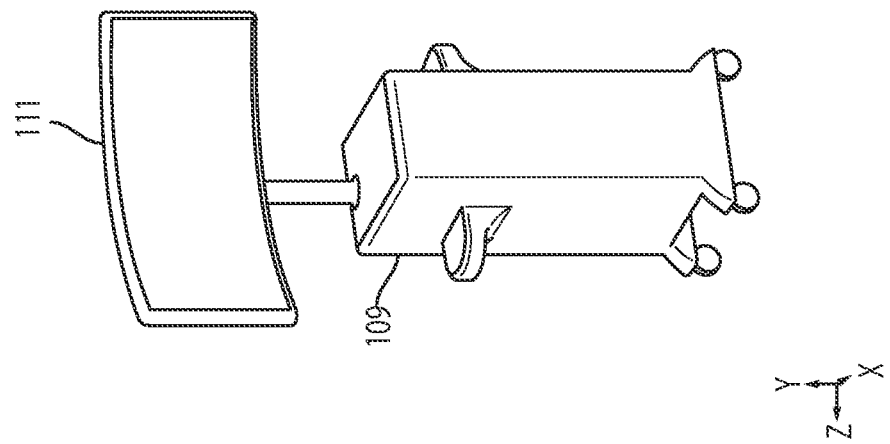
Figure 2B:
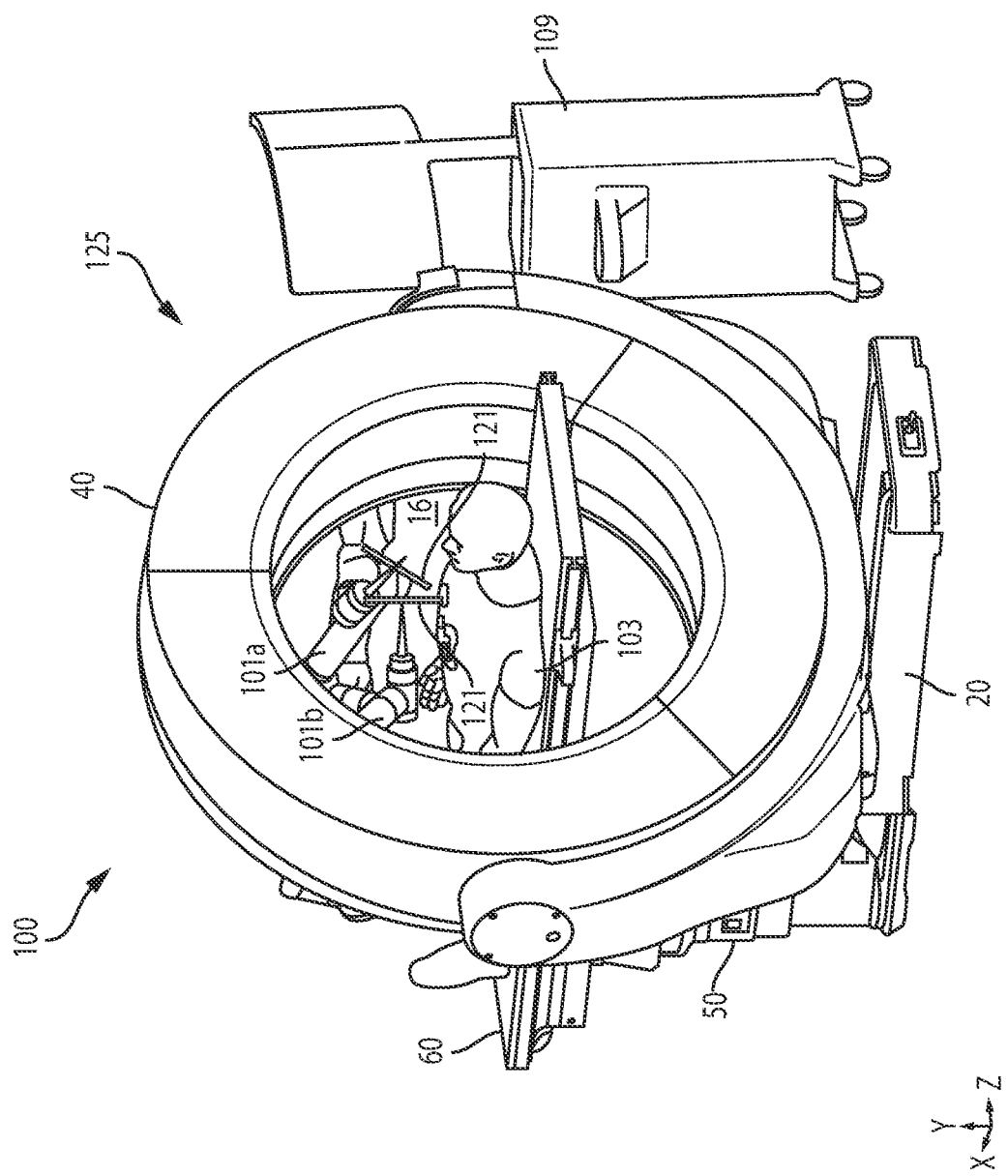
Figure 2C:
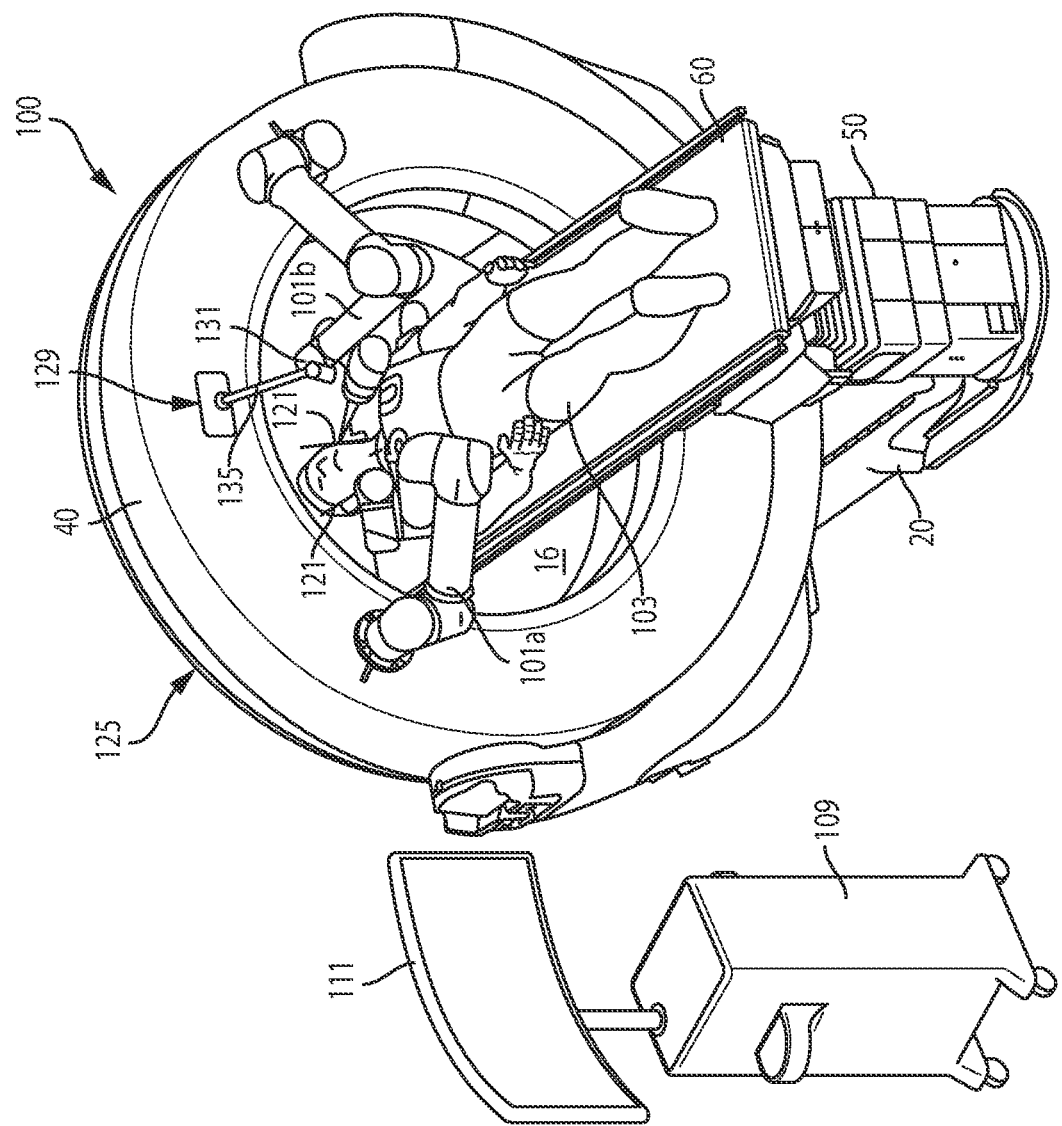

In embodiments, the imaging system 125 may be configured to move with respect to the patient 103. For example, at least a portion of the imaging system 125 (e.g., the gantry 40) may move with respect to the patient 103 to obtain images of a particular region of the patient's body, and may also be moved away from the region to facilitate a surgical procedure being performed within the region. In the embodiment shown in FIGS. 1A-1C, the patient support 60 on which a patient 103 may be located is secured to the base 20 of the imaging system 125 by the column 50, and the gantry 40 may translate with respect to the base 20, the column 50 and the patient support 60. This is illustrated in FIGS. 2A-2C, which show the gantry 40 translated on the base 20 so that a portion of the patient 103 and patient support 60 are located within the bore 16 of the gantry 40.

In the embodiment of FIGS. 1A-2C, the column 50 is located on a first end of the base 20 and the patient support 60 attached to the column 50 is cantilevered over the base 20 so that the gantry 40 may translate over substantially the entire length of the patient support 60. The gantry 40 is supported by a gimbal 30 that includes a pair of arms 31,33 that extend upwards from the base 20 and are connected to opposite sides of the gantry 40. The gimbal 30 may include bearing surfaces that travel on rails 23 on the base 20 to provide the translation motion of the gimbal 30 and gantry 40. A drive mechanism (not shown for clarity) may drive the translation of the gimbal 30 and gantry 40. An encoder or similar sensing device may determine the translation position of the gantry 40 on the base 20. In embodiments, the gantry 40 may tilt with respect to the gimbal 30.

In some embodiments, the patient support 60 and/or the column 50 may be translated as an alternative or in addition to translating the gantry 40 of the imaging system 125. For example, the patient support 60 may be translated with respect to the column 50, or the entire column 50 and patient support 60 may be translated with respect to the base 20. In this way, the patient 103 may be moved into and out of the bore 16 of the gantry 40. In some embodiments, the column 50 may be configured to raise and lower the height of the patient support 60 with respect to the base 20. The patient support 60 may also be rotatable with respect to the base 20, either by rotating the patient support 60 on the column 50 or by rotating the column 50 and patient support 60 with respect to the base 20.

The system 100 may also include a motion tracking apparatus 129 for tracking the position of at least one of the robotic arm(s) 101a, 101b and the imaging system 125 in three-dimensional space. The tracking apparatus 129 may also track the position of the patient 103 as well as other objects, such as the patient support 50 and/or surgical tools 122 within the surgical area. Various systems and technologies exist for tracking the position (including location and/or orientation) of objects as they move within a three-dimensional space. Such systems may include a plurality of active or passive markers fixed to the object(s) to be tracked and a sensing device that detects radiation emitted by or reflected from the markers. A 3D model of the space may be constructed in software based on the signals detected by the sensing device.

In the embodiment shown in FIGS. 1A-2C, the motion tracking apparatus 129 is an optically-based motion tracking apparatus that includes an optical sensor (i.e. camera) 131 and one or more markers 133. In this embodiment, the camera 131 is attached to the gantry 40 of the imaging device 125 and is oriented such that the camera 131 may look directly into the sterile surgical field. In other embodiments, the camera 131 may be mounted to another portion of the imaging device 125 or to another component of the system 100, such as the patient support 60, or may be mounted to a separate support structure. An advantage of the configuration shown in FIGS. 1A-2C is that the camera 131 may look down directly into the surgical field without being blocked. In embodiments, the camera 131 may be mounted to the end of an arm 135 that may include actuator(s) for moving the camera 131 so that the surgical field is maintained within the camera's field of view. For example, as the gantry 40 moves (e.g., translates) with respect to the patient 103, the camera 131 may swivel on the arm 135 and/or the arm 135 itself may pivot, bend, extend and/or contract to maintain the surgical field within the field of view of the camera 131.

The markers 133 may comprise any active or passive marker that may be detected by the camera 131. The markers 133 may be fixed to various objects to be tracked, such as the end effectors 121 of the robotic arms 101a, 101b, as shown in FIG. 1C. One or more markers 133 may also be attached to surgical tools 122 to enable the position and orientation of the various surgical tools 122 within the surgical field to be tracked in real time during a surgical procedure. One or more markers 133 may also be attached to other objects, such as the patient 103, the patient support 60 and/or the imaging device 125. In embodiments, the markers 133 may be moire pattern markers that may provide measurement data for position and orientation using a single camera 131 using Moire Phase Tracking (MPT) technology. Each marker 133 may also include a unique identifier or code that may enable different objects within the camera's field of view to be uniquely identified and tracked. An example of an MPT-based tracking system is available from Metria Innovation Inc. of Milwaukee, Wisconsin.

Figure 3:
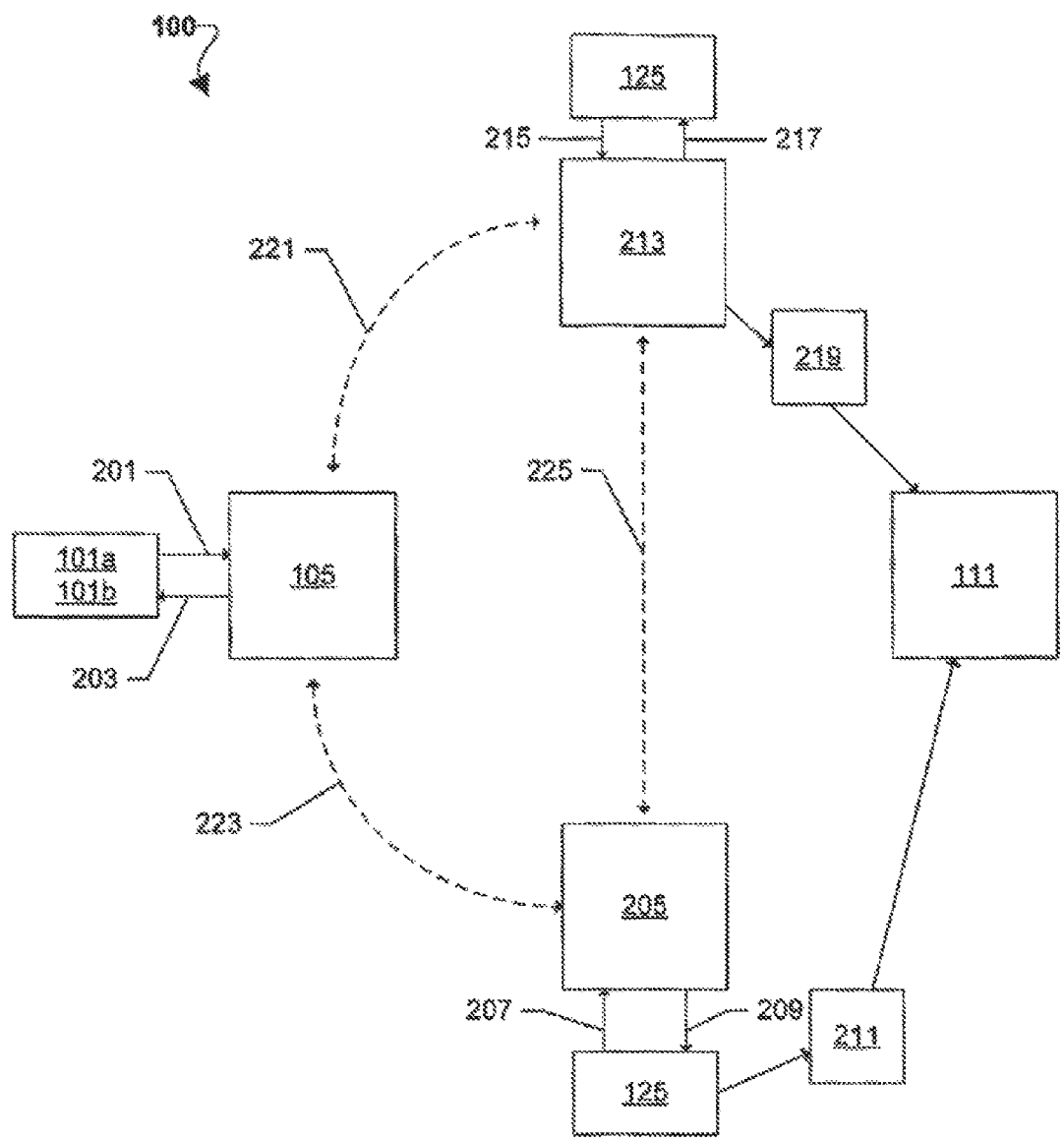
FIG. 3 is a system block diagram that schematically illustrates various components of a system for performing robotically-assisted surgery according to one embodiment.

FIG. 3 is a system block diagram that schematically illustrates various components of the system 100 according to one embodiment. As discussed above, a first controller 105 may control the operation of one or more robotic arms 101a, 101b. The first controller 105 may receive feedback data (indicated by arrow 201) from the robotic arm(s) 101a, 101b regarding the status and operation of the arms 101a, 101b. The feedback data may include sensor (e.g., encoder) data that may be used to determine the position and orientation of each of the joints 115 of the robotic arms 101a, 101b. The first controller 105 may send control signals (indicated by arrow 203) to the robotic arm(s) 101a, 101b to control the movements of the arms 101a, 101b.

The system 100 may also include a second controller 205 for controlling the operation of the imaging device 125. The second controller 205 may receive feedback data (indicated by arrow 207) regarding the status and operation of the imaging device 125. The feedback data may include information as to the position and orientation of the imaging device 125, such as the position (translation or tilt) of the gantry 40 and/or the position of the patient support 60. The second controller 205 may also send control signals (indicated by arrow 209) to various components of the imaging device 125 to control the operation of the imaging device 125, including controlling the imaging device 125 to obtain image data 211 (e.g., a three-dimensional CT reconstruction) of an object located within the bore 16 of the gantry 40. The image data 211 may be displayed on a display 111.

The system 100 may also include a third controller 213 for controlling the operation of the motion tracking apparatus 129. The third controller 213 may receive data sensed by the camera 131 (indicated by arrow 215) and based on this data may determine position and/or orientation data for each of the markers 133 within the field of view of the camera 131. Based on the determined position and/or orientation of the markers 133, a three-dimensional model 219 of various objects within the surgical space (e.g., the patient 103, surgical tool(s) 122, the end effector(s) 121 of the robotic arm(s) 101a, 101b, the imaging device 125, etc.) may be generated. The third controller 213 may also send control signals (indicated by arrow 217) to the camera 131 to control the operation of the camera 131, such as by adjusting the camera's field of view.

The first, second and third controllers 105, 205, 213 may communicate and share various data with one another, as indicated by arrows 221, 223 and 225. The sharing of data including positional data enables the controllers to operate in a common coordinate system. For example, the image data 211 of the patient 103 obtained by the imaging device 125 may be registered to the position data obtained by the motion tracking apparatus 129, as is known in the field of surgical navigation systems. The position of one or more objects tracked by the motion tracking apparatus 129 may be shown on the display 111, such as overlaying the display of image data 211 from the imaging device 125. Further, the first controller 105 may determine the position of the robotic arm(s) 101a, 101b with respect to the rest of the system 100 based on position data from the motion tracking apparatus 129 and/or the imaging device 125.

In embodiments, each of the controllers 105, 205, 213 may comprise separate computing devices, each including a memory and processor for performing the various functions described herein. The separate computing devices may communicate with one another via a suitable data link (e.g., Ethernet). In other embodiments, two or more of the controllers 105, 205, 213 may be integrated in a single computing device.

A system 100 as described above may be used for performing surgical procedures on a patient 103, which may be a human or animal patient. For example, the patient 103 may be provided on a patient support 60 (e.g., a surgical table), and the imaging device 125 may be used to obtain images of the patient 103, such as a CT scan of a particular region of the patient's anatomy. This may include moving the gantry 40 of the imaging device 125 (e.g., translating the gantry 40 on the base 20) so that a region of interest of the patient 103 is located within the bore 16 of the gantry 40 and operating the imaging components (e.g., x-ray source and detector) to obtain image data of the patient 103. Alternately, the patient 103 may be moved into the bore 16, such as by translating the patient support 60 into the bore 16 of the gantry 40.

The image data obtained by the imaging device 125 may be displayed on a display, such as the display 111 on the mobile cart 109 shown in FIGS. 1A-2C. In embodiments, a surgeon or other clinician may interact with the image data shown in the display 111 using a suitable user interface/input device 110 (e.g., keyboard, mouse, touchpad, trackball, touchscreen, etc.). The clinician may be able to modify the image data displayed on the screen of the display 111, such as by zooming in or out of a particular region, selecting or changing the particular projection angle(s) or slices in the case of a three-dimensional tomographic reconstruction.

Figure 4:
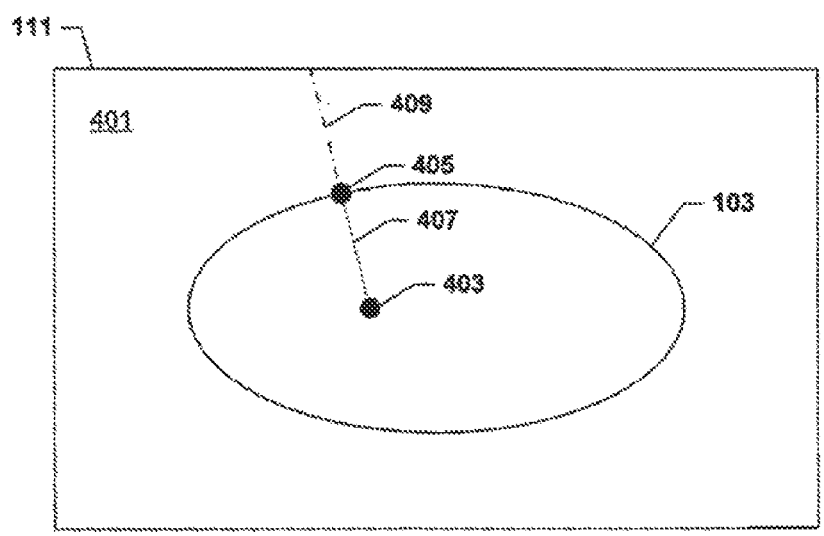
FIG. 4 schematically illustrates a method of defining a trajectory for insertion of a surgical tool into a patient's body using image data.

In embodiments, a surgeon/clinician may also select particular points on the displayed image using an input device. This is schematically illustrated in FIG. 4, which shows a display 111 that displays an image 401 (e.g., a cross-sectional slice) of a region of interest of a patient 103 obtained using an imaging device 125. The surgeon/clinician may identify and select at least one target point 403 in the displayed image 401. The target point 403 may represent an end point for the insertion of a particular surgical tool 122 into the patient's body during a surgical procedure. The surgeon/clinician may also identify and select at least one entrance point 405 on the displayed image 401. The entrance point 405 may represent a point on the exterior of the patient's body (e.g., the skin) through which the surgeon will insert the particular surgical tool 122. The target point 403 and corresponding entrance point 405 thus define a unique trajectory 407 through the body of the patient 103, as schematically illustrated by the dashed line in FIG. 4. In embodiments, the surgeon may select the entrance point 405 and the trajectory 407 within the patient's body in order to facilitate the insertion of the surgical tool 122 to the target point 403 while minimizing damage to other tissue or organs of the patient 103. As also shown in FIG. 4, the trajectory 407 may also be extended outside of the patient's body to define a unique vector 409 in three-dimensional space extending from the selected entrance point 405, as indicated by the dashed-dotted line in FIG. 4.

Figure 5:
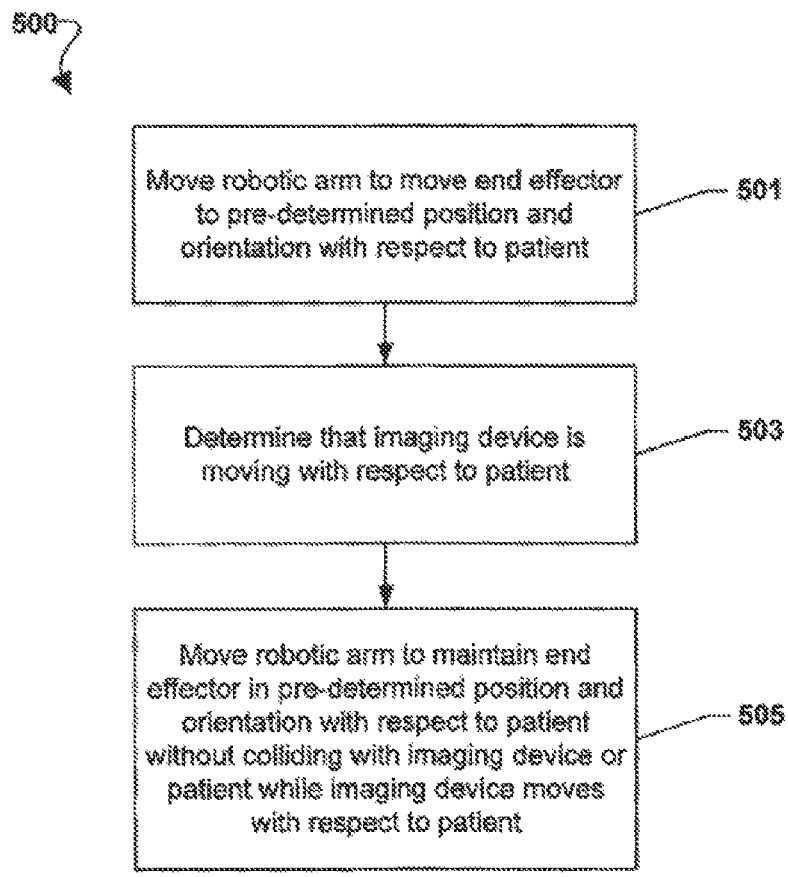
FIG. 5 is a process flow diagram illustrating a method for operating a robotic arm to perform robotically-assisted surgery according to an embodiment.

FIG. 5 is a process flow diagram that illustrates a method 500 for operating a robotic arm 101 to perform robotically-assisted surgery according to one embodiment. The method 500 may be performed using the system 100 described above with reference to FIGS. 1A-4. For example, the system 100 may include at least one robotic arm 101a, 101b having an end effector 121. The end effector 121 may comprise a hollow tube or cannula, as described above. Each of the robotic arms 101a, 101b may be moveable with respect to a patient 103 and an imaging device 125, where at least a portion of the imaging device 125, such as a gantry 40, is moveable with respect to the patient 103 to obtain imaging data of the patient 103. The system 100 may also include a controller 105 for controlling the movements of the at least one robotic arm 101a, 101b.

In block 501 of method 500, the controller 105 may control the at least one robotic arm 101 to move the end effector 121 of the robotic arm 101 to a pre-determined position and orientation with respect to the patient 103. The pre-determined position and orientation may be based on imaging data obtained by the imaging system 125. For example, the imaging data may be used to determine a unique vector 409 in three-dimensional space corresponding to a desired insertion trajectory 407 for a surgical tool, as described above with reference to FIG. 4. The controller 105 of the at least one robotic arm 101a, 101b may translate this vector 409 into a coordinate system used for controlling the position and movement of the robotic arm 101a, 101b based on positional information received from the imaging device 125 and/or from a motion tracking apparatus 129, as described above with reference to FIG. 3. The controller 105 may move the at least one first robotic arm 101a, 101b so that the end effector 121 of the robotic arm 101a, 101b is oriented along a pre-defined vector 409. For example, as shown in FIG. 1A, the end effector 121 of a first robotic arm 101a is oriented along a first vector 409a. The end effector 121 of a second robotic arm 101b is oriented along a second vector 409b. Each of the end effectors 121 may be positioned adjacent to a desired entrance point 405 for a surgical tool. A surgeon may then perform an invasive surgical procedure, which may include inserting one or more surgical tools through the end effectors 121 and into the body of the patient 103. The position and orientation of the end effectors 121 may ensure that the surgical tools 121 follow the desired trajectory 407 (see FIG. 4) through the patient's body to reach the target area.

In embodiments, a motion tracking apparatus 129 such as described above may be configured to track the at least one robotic arm 101a, 101b to ensure that the end effector(s) 121 maintain the pre-determined position and orientation with respect to the patient 103. If an end effector 121 moves from the pre-determined position and orientation (e.g., due to the robotic arm being accidentally bumped), the motion tracking apparatus 129 may detect this movement and alert the surgeon or other clinician. Alternately or in addition, the motion tracking apparatus 129 may send a message to the controller 105 of the at least one robotic arm 101a, 101b indicating a detected deviation from the pre-determined position and orientation of the end effector 121. The controller 105 may then move the robotic arm 101a, 101b to compensate for the detected deviation. In some embodiments, the motion tracking apparatus 129 may also track the patient 103 (e.g., where a plurality of markers 133 are placed on the patient 103) to determine whether the patient 103 has moved relative to the end effector 121. The motion tracking apparatus 129 may notify the surgeon when the patient 103 moves by more than a predetermined amount. In some embodiments, the motion tracking apparatus 129 may send message(s) to the controller 105 of the robotic arms(s) 101a, 101b regarding detected movements of the patient 103. Such movements may include, for example, motion of the patient 103 corresponding to the patient's breathing. The controller 105 may move the robotic arm(s) 101a, 101b to compensate for any such movement (e.g., to maintain the end effector 121 in the same position and orientation with respect to the selected entrance point 405 on the patient's body).

During a surgical procedure, the motion tracking apparatus 129 may also be used to track a variety of objects, including surgical tools 122, within the surgical area. For example, as discussed above, various surgical tools 122 may be provided with markers 122 that enable the motion tracking system 129 to identify the tools and continually track their movements in three-dimensional space. Thus, as a tool 122 is inserted through an end effector 121 and into the patient's body, the motion tracking system 129 may use the detected position of the marker(s) 133 and a known geometry of the tool 122 to determine the depth of insertion of the tool 122 into the body. This may be displayed on the display 111 of the system 100 (e.g., overlaying the image data previously obtained from the imaging device 125) and may aid the surgeon in determining whether the surgical tool 122 has been inserted to the desired depth in the patient's body.

In block 503 of method 500, the controller 105 may determine that at least a portion of the imaging device 125 is moving with respect to the patient 103. For example, after obtaining imaging data of the patient 103, the gantry 40 of the imaging device 125 may be translated away from the surgical area as shown in FIGS. 1A-1C to provide easier access to the surgical area for performing a surgical procedure. The robotic arm(s) 101a, 101b may then be moved to a first position as shown in FIGS. 1A-1C, with the end effector(s) 121 arranged in a pre-determined position and orientation with respect to the patient 103. At a later time, the surgeon may wish to obtain additional image data of the patient 103 (e.g., to confirm the location of a surgical tool 122 within the patient 103), and the gantry 40 may be translated back over the surgical area such as shown in FIGS. 2A-2C to perform an updated imaging scan.

Alternately, following the initial imaging scan, the robotic arm(s) 101a, and 101b may be moved into position on the patient 103 as shown in FIGS. 1A-1C while the gantry 40 is still located over the surgical area. The gantry 40 may then be moved (e.g., translated) out of the surgical area as shown in FIGS. 2A-2C before performing the surgical procedure.

In either case, the controller 105 may determine that at least a portion of the imaging device (e.g., the gantry 40) is moving with respect to the patient 103 based on a signal that may be received, for example, from the imaging device 125, the motion tracking system 129 and/or from a user via a user input mechanism.

In block 505 of method 500, the controller 105 may control the at least one robotic arm 101a, 101b to move a first portion of the at least one robotic arm 101a, 101b while the imaging device 125 moves with respect to the patient 103 while maintaining the end effector 121 of the arm in the pre-determined position and orientation (e.g., vector 409) with respect to the patient 103. Thus, in an embodiment such as shown in FIGS. 1A-2C, where the first end 117 of the arm 101 is attached to the portion of the imaging device 125 that moves with respect to the patient 103 (i.e., the gantry 40), the controller 105 may control the movements of the arm 101 such that as the first end 117 of the arm moves towards or away from the patient 103, the end effector 121 maintains its original position and orientation with respect to the patient 103.

In embodiments, the controller 105 may control the movement of the first portion of the arm 101a, 101b such that the arm 101a, 101b does not collide with either the imaging device 125 or the patient 103 during the movement of the arm. For example, as the imaging device 125 and robotic arms 101a, 101b move from the position as shown in FIGS. 1A-1C to the position as shown in FIGS. 2A-2C, at least a portion of the arms 101a, 101b including the end effectors 121 are located inside the bore 16 of the gantry 40.

The controller 105 may control the movement of each of the arms 101a, 101b so that as the gantry 40 advances towards the patient, none of the joints 115 of the arms 101a, 101b collide with the side wall or inner diameter of the ring or with the patient 103. The controller 105 may control the movement(s) of the arm(s) 101a, 101b in accordance with a motion planning algorithm that utilizes inverse kinematics to determine the joint parameters of the robotic arm that maintain the position and orientation of the end effector 121 while avoiding collisions with the imaging device 125 and the patient 103.

In embodiments, the controller 105 may determine the position of each of the robotic arms 101*a*, 101*b* in relation to the gantry 40 based on position data received from the imaging device 125 (e.g., indicating the translation and/or tilt position of the gantry 40 with respect to the base 20). Alternately or in addition, the controller 105 may utilize position information received from the motion tracking apparatus 125. As discussed above, the motion tracking system 129 may be used to construct a three-dimensional model (e.g., a CAD model) of the various objects being tracked by the motion tracking apparatus 129. The sharing of data between the robotic system, the imaging device and the motion tracking apparatus may enable these systems to operate in a common coordinate system.

In some embodiments, the position of the patient 103 may be defined using a freehand technique. For example, prior to commencement of the surgical procedure, the surgeon or other clinician may use the second (i.e., distal) end 119 of a robotic arm 101 to manually trace across the external surface of the patient 103, such as around the surgical area. This may be used to define a three-dimensional boundary surface in the common coordinate system into which no portion of the at least one robotic arm 101*a*, 101*b* may enter. This technique may also be used to define boundary surfaces corresponding to other objects and components of the system 100 proximate to the surgical area, such as the patient support 60 or portions of the imaging system 125. In other embodiments, the motion tracking apparatus 129 may be used to define the boundary surface corresponding to the patient 103, such where a plurality of markers 133 are placed in different locations on the patient 103 proximate to the surgical area and are tracked by the camera 131. The positions of the markers 133 tracked by the motion tracking apparatus 129 may be used to define a three-dimensional boundary surface into which the robotic arm 101*a*, 101*b* may not enter.

In some cases, the controller 105 of the at least one robotic arm 101*a*, 101*b* may determine that it is not possible to move a robotic arm without either changing the position or orientation of the end effector 121 with respect to the patient 103, or some part of the arm colliding with the imaging device 125 or the patient 103. For example, a translation of the gantry 40 may result in the arm 101 being extended beyond its maximum length. In other cases, the controller 105 may determine that no set of joint movements are possible to avoid collisions while maintaining the end effector in a fixed position and orientation. In such a case, the controller 105 may issue an alert that may be perceived by the surgeon or other clinician, and may preferably also send a signal to the imaging device 125 to stop the motion of the gantry 40.

As the gantry 40 moves with respect to the patient 103, the camera 131 may also move to maintain the surgical area within the field-of-view of the camera 131. In the embodiment of FIGS. 1A-2C, for example, where the camera 131 is attached to the gantry 40 by arm 135, the camera 131 may include an actuator (e.g., a DC motor-based actuator) that causes the camera 131 to pivot on the arm 135 to keep the camera 131 pointed down into the surgical area while the camera 131 moves with the gantry 40. This may enable the motion tracking apparatus 129 to continually track the position of objects within the surgical area as the gantry 40 and robotic arms 101*a*, 101*b* move. Thus, the motion tracking apparatus 129 may provide a redundant safety feature in that if the motion tracking apparatus 129 detects a movement of an end effector 121 from the predetermined position and orientation with respect to the patient 103, the surgeon or other clinicians may be promptly notified. In embodiments, when the motion tracking apparatus 129 detects a change in position or orientation of the end effector 121 with respect to the patient 103 by more than a threshold amount, the motion tracking apparatus 129 may send a message to the imaging system 125 and the controller 105 of the robotic arm(s) to stop all motion of the system 100.

When the gantry 40 is moved such that the patient 103 is located in the bore 16 of the gantry 40, the imaging device 125 may be operated to obtain imaging data of the patient 103 (e.g., a CT scan of at least a portion of the patient 103). The system 100 may therefore be configured as shown in FIGS. 2A-2C, with the gantry 40 moved over the surgical area and at least a portion of the robotic arms 101*a*, 101*b* including the end effectors 121 are located within the bore 16. In embodiments, the end effectors 121 may comprise a radiolucent material so as not to block x-rays. The updated image data may be shown on the display 111, and may enable the surgeon to confirm the location of a surgical tool 122 inserted into the patient 103. After the image(s) are acquired by the imaging device 125, the gantry 40 may be moved out of the surgical area, such as by translating the gantry 40 to the position as shown in FIGS. 1A-1C. The controller 105 of the robotic arms 101*a*, 101*b* may again control the robotic arms to maintain the predetermined position and orientation of the end effectors 121 with respect to the patient 103 while the gantry 40 translates with respect to the patient.

An alternative embodiment of a system 100 for robotically-assisted surgery is shown in FIGS. 6A-6C and 7A-7C. The system 100 in this embodiment is substantially identical to the system 100 described above with reference to FIGS. 1A-2C. This embodiment differs from the embodiments described above in that there is a single robotic arm 101 (rather than the pair of arms 101*a*, 101*b* shown in FIGS. 1A-2C).

Similar to the embodiment of FIGS. 1A-2C, the robotic arm 101*a* and the camera 131 for the motion tracking system 129 are attached to the gantry 40 of the imaging device 125. However, in this embodiment, the robotic arm 101 and the camera 131 are attached to the side of the gantry that faces away from the patient 103.

Figure 7A:
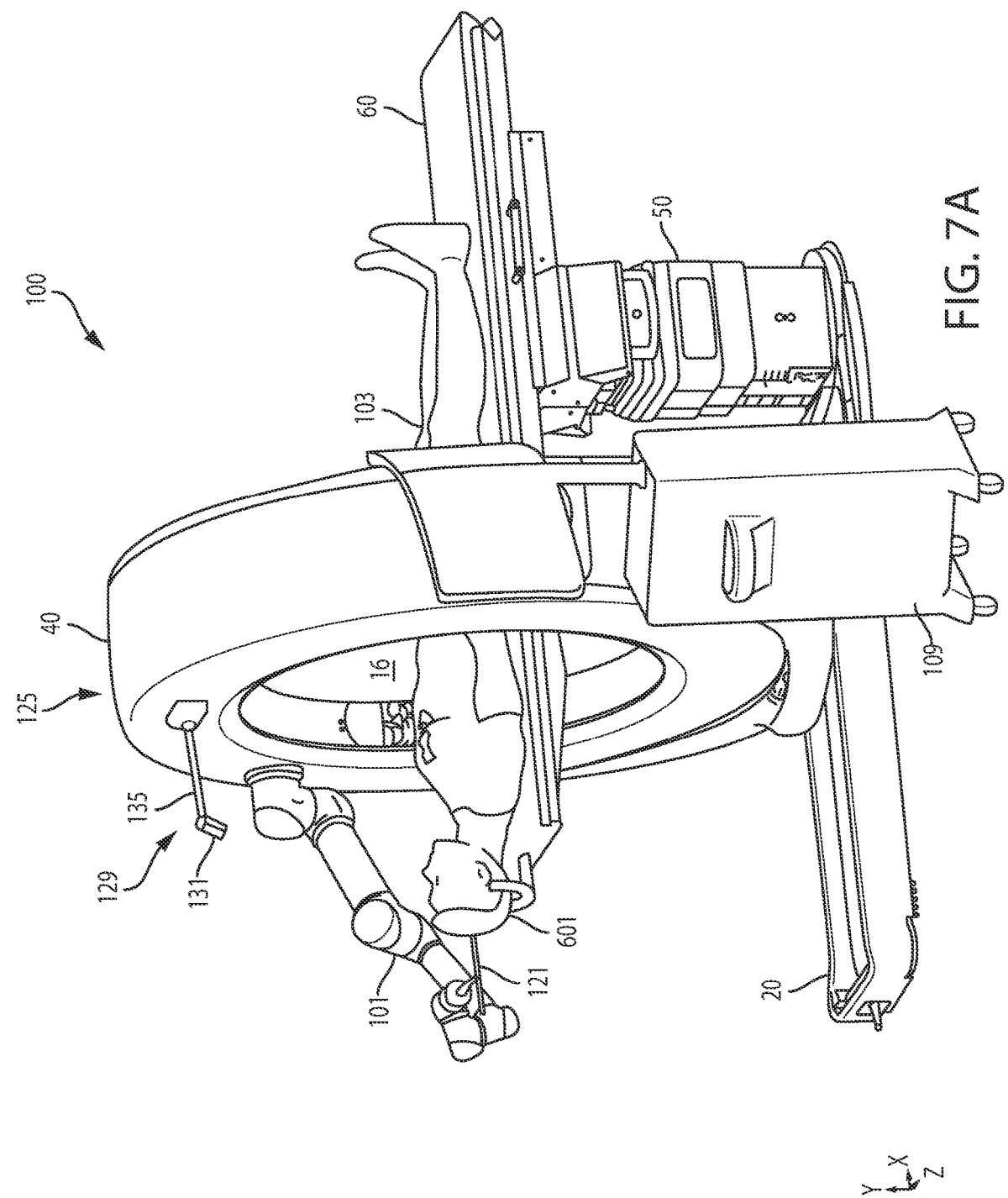
Figure 7B:
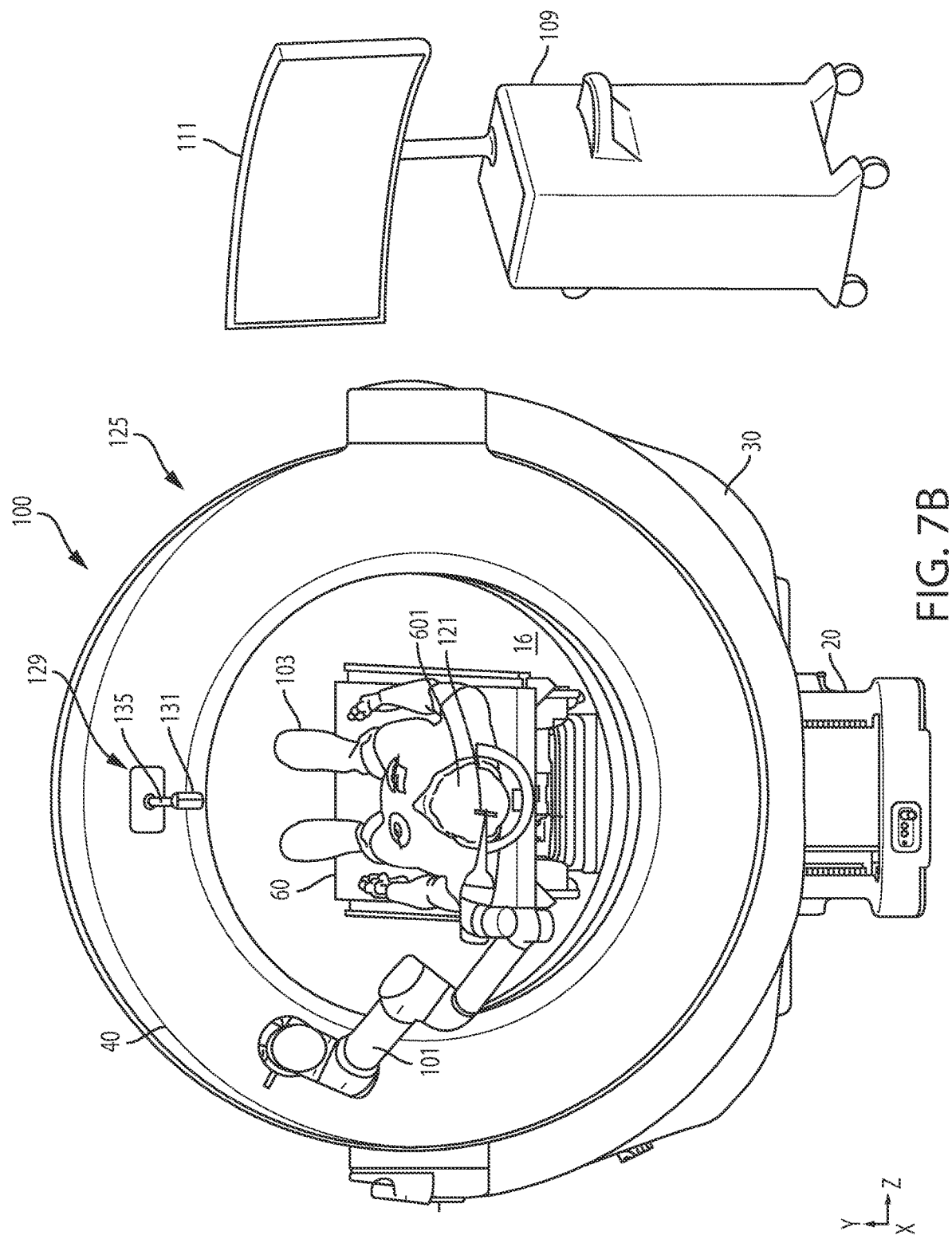
Figure 7C:
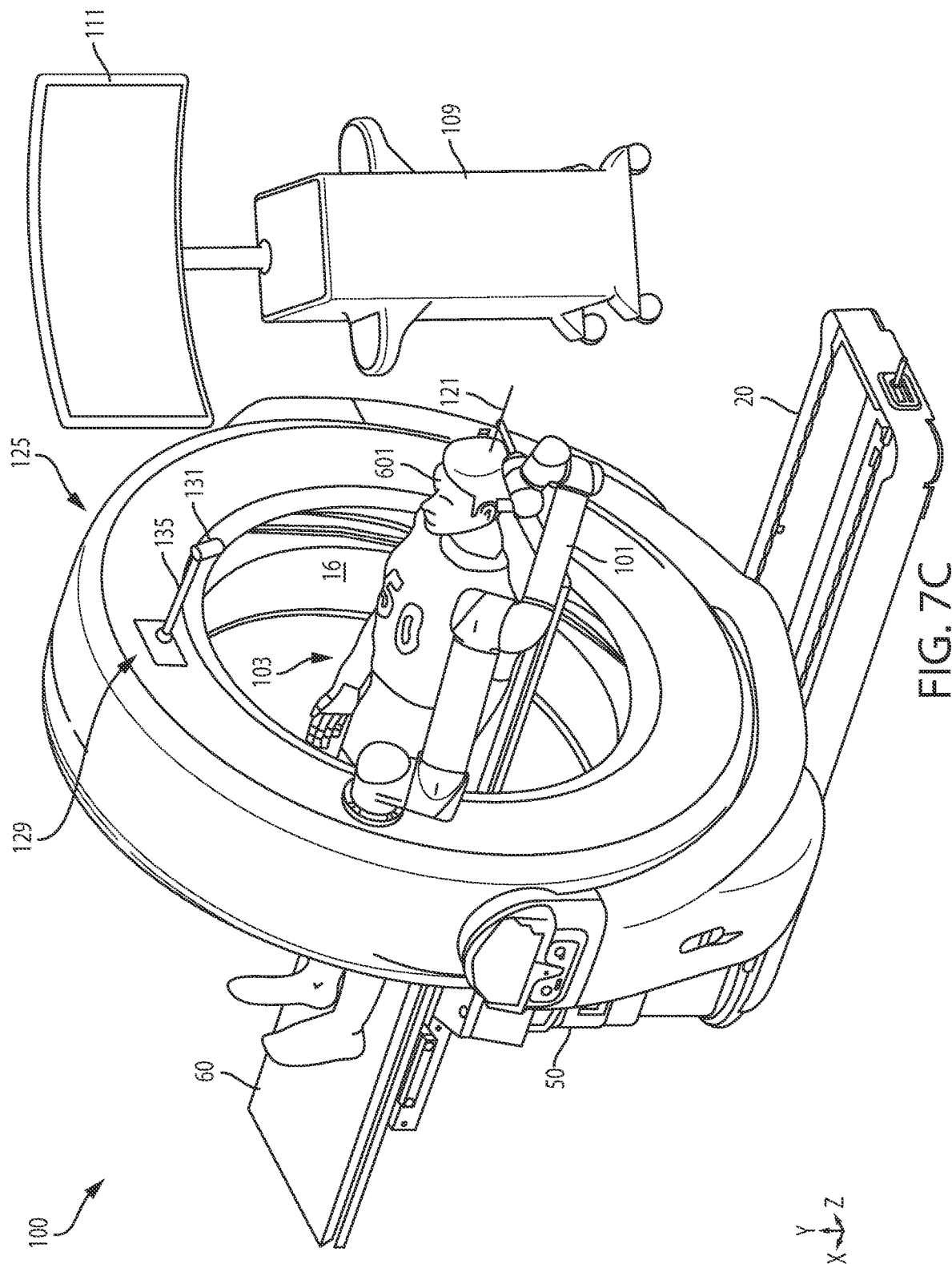

The configuration as shown in FIGS. 6A-6C and 7A-7C may be advantageously used, for example, for a cranial surgical procedure (e.g., neurosurgery, deep brain stimulation, insertion of an external ventricular drain, etc.). As shown in FIGS. 6A-6C, for example, the head 601 of the patient 103 may be stabilized at one end of the patient support 60. The head 601 may be located within the bore 16 of the gantry 40 of the imaging device 125 for obtaining pre-operative or intra-operative image data. The robotic arm 101 may be moved to a position such that the end effector 121 is in a predetermined position and orientation with respect to the patient 103, as described above. The gantry 40 may be moved down along the length of the patient's body to provide easier access to the surgical area, as shown in FIGS. 7A-7C. The controller 105 of the robotic arm 101 may control the movements of robotic arm 101 such that the end effector 121 is maintained in the pre-determined position and orientation with respect to the patient 103 while the gantry 40 moves. As shown in FIGS. 7A-7C, this may include a stretching out or unfolding of the arm. Similarly, as the gantry 40 translates towards the head 601 of the patient 103 the joints of the arm 101 may be folded up as shown in FIGS. 6A-6C. In either case, the controller 105 of the robotic arm 101 may use inverse kinematics to ensure that the position and orientation of the end effector 121 with respect to the patient 103 is maintained without any portion of the arm 101 colliding with either the imaging device 125 or the patient 103.

As shown in FIGS. 6A-7C, the camera 131 of the motion tracking apparatus 129 and/or the arm 135 to which the camera 131 is attached may move in response to the movement of the gantry 40 to maintain the surgical area within the field-of-view of the camera 131.

Yet another embodiment of a system 100 for robotically-assisted surgery is shown in FIGS. 8A-8D and 9A-9B. The system 100 in this embodiment is substantially identical to the system 100 as previously described. This embodiment differs from those described above in that a pair of robotic arms 101a, 101b are attached to the patient support 60 rather than to the gantry 40 of the imaging device 125. The camera 131 for the motion tracking system 129 is attached to the gantry 40 of the imaging device 125. The robotic arms 101a, 101b may be attached at any suitable location on the patient support 60, such as on surgical rails 801 that extend along the sides of the patient support 60. In embodiments, an adaptor 803 may be secured to a surgical rail 801, and the robotic arm may be snapped into or otherwise secured to the adaptor.

The operation of the embodiment shown in FIGS. 8A-8D and 9A-9B may be similar to the previous embodiments. FIGS. 8A-8D show the gantry 40 translated over the surgical area and FIGS. 9A-9B show the gantry 40 translated away from the surgical area in order to allow the surgeon access to the surgical area. In this embodiment, the robotic arms 101a, 101b are attached proximate to the distal end of the patient support 60 (i.e., opposite the support column 50). Thus, as shown in FIGS. 8A-8D and 9A-9B, the robotic arms 101a, 101b extend into or through the bore 16 of the gantry 40 in order to move the end effectors 121 to the pre-determined position and orientation with respect to the patient 103.

A difference between the embodiment shown in FIGS. 8A-8D and the previous embodiments is that because the robotic arms 101a, 101b are attached to the patient support 60 rather than the gantry 40, the robotic arms 101a, 101b may not need to move with respect to the patient 103 once the end effectors 121 are moved to the predetermined position and orientation. The controller 105 of the robotic arms 101a, 101b may move the end effectors 121 to the pre-determined position and orientation such as shown in FIGS. 8A-8D and 9A-9B without colliding the arms 101a, 101b with either the imaging system 125 or the patient 103. The arms 101a, 101b may be moved to a configuration such that they will not collide with the gantry 40 as the gantry 40 moves (e.g., translates) with respect to the patient 103, such as between the positions shown in FIGS. 8A-8D and 9A-9B, respectively. Alternately, the arms 101a, 101b may be moved to an initial configuration with the end effectors 121 in the pre-determined position and orientation with respect to the patient 103, and a portion of the arm(s) 101a, 101b may be moved to avoid colliding with the gantry 40 and the patient 103 while maintaining the position and orientation of the end effectors 121 when the gantry 40 moves with respect to the patient.

In this embodiment, the camera 121 of the motion tracking apparatus 129 is attached to the gantry 40 by arm 135. As shown in FIGS. 8A-8D and 9A-9B, the camera 131 and/or the arm 135 may move in response to the movement of the gantry 40 to maintain the surgical area within the field-of-view of the camera 131.

Yet another embodiment of a system 100 for robotically-assisted surgery is shown in FIGS. 10A-10C and 11A-11C. In this embodiment, the patient support 60 is configured for a patient 103 in a seated position. A robotic arm 101 and a camera 131 for the motion tracking apparatus 129 are both mounted to the patient support 60. In this embodiment, the robotic arm 101 and camera 131 are attached to surgical rails 801 extending along opposite sides of the patient support 60. FIGS. 10A-10C show the gantry 40 of the imaging device 125 translated away from the patient 103, and FIGS. 11A-11C show the gantry 40 translated to the patient 103 such that the surgical area is located within the bore 16. The gantry 40 is tilted with respect to the gimbal 30 in this embodiment.

The operation of the system 100 in the embodiment shown in FIGS. 10A-10C and 11A-11B may be substantially identical to the embodiments described above. The robotic arm 101 may be moved to a position such that the end effector 121 is in a predetermined position and orientation with respect to the patient 103, as described above. The camera 131 and arm 135 may be positioned such that the camera 131 is looking into the surgical area. If an imaging scan is desired, the gantry 40 which is tilted on the gimbal 30 may be translated towards the patient 103, such as shown in FIGS. 11A-11C. The controller 105 of the robotic arm 101 may use inverse kinematics to move the robotic arm 101 to maintain the position and orientation of the end effector 121 with respect to the patient 103 without any portion of the arm 101 colliding with either the imaging device 125 or the patient 103.

In some embodiments, the patient support 60 may be rotatable with respect to the imaging device 125, such as shown in FIGS. 12A-12B, which may provide the surgeon with additional space for performing a surgical procedure. FIGS. 12A-12B show the patient support 60 rotated 90° with respect to the imaging device 125. When an additional imaging scan is desired, the patient support 60 may be rotated back to the position as shown in FIGS. 10A-10C, and the gantry 40 may be translated over the patient 103 to obtain the imaging scan, as shown in FIGS. 11A-11C. In this embodiment, the robotic arm 101 is mounted to the patient support 60 and thus moves with the patient support 60 as it rotates. In other embodiments, the robotic arm 101 may be mounted to another structure, such as the imaging device 125 or to a separate support structure, and the controller 105 of the robotic arm 101 may be configured to move the robotic arm 101 to maintain the end effector 121 in the pre-determined position and orientation with respect to the patient 103 as the patient support 60 rotates.

As discussed above, the robotic arm 101 may be attached anywhere on the system 100, such as the on the gantry 40, the patient support 60, the support column 50, the base 20 or the gimbal 30. Mounting a robotic arm on the gimbal 30 may enable the robotic arm 101 to remain in close proximity to the gantry 40 and easily extend into the bore 16 of the gantry 40 without the weight of the robotic arm 101 being distributed onto the gantry 40 itself, which may be weight balanced. In addition, attaching the robotic arm 101 to the gimbal 30 may enable the gantry 40 to be tilted with respect to the patient without also tilting the first end 117 of the robotic arm 101 with respect to the patient. One or more robotic arms 101 may be mounted directly to the gimbal 30 (e.g., proximate to the end(s) of one or both of the arms 31,33 that attach to opposing sides of the gantry 40). Alternately, a plate or other support member may be attached to and extend from an arm 31, 33 of the gimbal 30, and the robotic arm 101 may be mounted to the plate/support member.

In an embodiment shown in FIGS. 13A-13D, a support member 1300 may extend from the gimbal 30 (e.g., from the end of an arm 31, 33 of the gimbal 30) and at least one robotic arm 101 may be mounted to the support member 1300. In embodiments, the support member 1300 may extend at least partially around an outer circumference of the gantry 40. In the embodiment of FIGS. 13A-13D, the support member 1300 comprises a curved rail that extends around the outer circumference of the gantry 40. In this embodiment, the support member 1300 forms a semicircular arc that extends between the ends of the respective arms 31 and 33 of the gimbal 30. The semicircular support member 1300 may be concentric with the outer circumference of the gantry 40.

A bracket mechanism 1301 may be located on the support member 1300 and may include a mounting surface 1303 for mounting the first end 117 of the robotic arm 101 to the bracket mechanism 1301. As shown in FIGS. 13A-13D, the mounting surface 1303 may project from the side of the support member and may be upwardly angled as shown in FIGS. 13A-13D. This may provide additional clearance for the "tilt" motion of the gantry 40 relative to the gimbal 30.

The bracket mechanism 1301 and the robotic arm 101 attached thereto may be moved to different positions along the length of support member 1300 (e.g., any arbitrary position between the ends of the arms 31, 33 of the gimbal 30) and may be fixed in place at a particular desired position along the length of the support member 1300. This is schematically illustrated in FIGS. 13C and 13D which are perspective and front views of the system 100 illustrating the bracket mechanism 1301 and the robotic arm 101 in a first position and a second position (indicated by phantom) on the support member 1300. In some embodiments, the bracket mechanism 1301 may be moved manually (e.g., positioned by an operator at a particular location along the length of the support member 1301 and then clamped or otherwise fastened in place). Alternately, the bracket mechanism 1301 may be automatically driven to different positions using a suitable drive mechanism (e.g., a motorized belt drive, friction wheel, gear tooth assembly, cable-pulley system, etc., not shown in FIGS. 13A-13D). The drive mechanism may be located on the bracket mechanism 1301, the support member 1300 and/or the gimbal 30, for example. An encoder mechanism may be utilized to indicate the position of the bracket mechanism 1301 and the first end 117 of the robotic arm 101 on the support member 1300. Although the embodiment of FIGS. 13A-13D illustrates one robotic arm 101 mounted to the support member 1300, it will be understood that more than one robotic arm may be mounted to the support member 1300 via respective bracket mechanisms 1301.

Figure 13A:
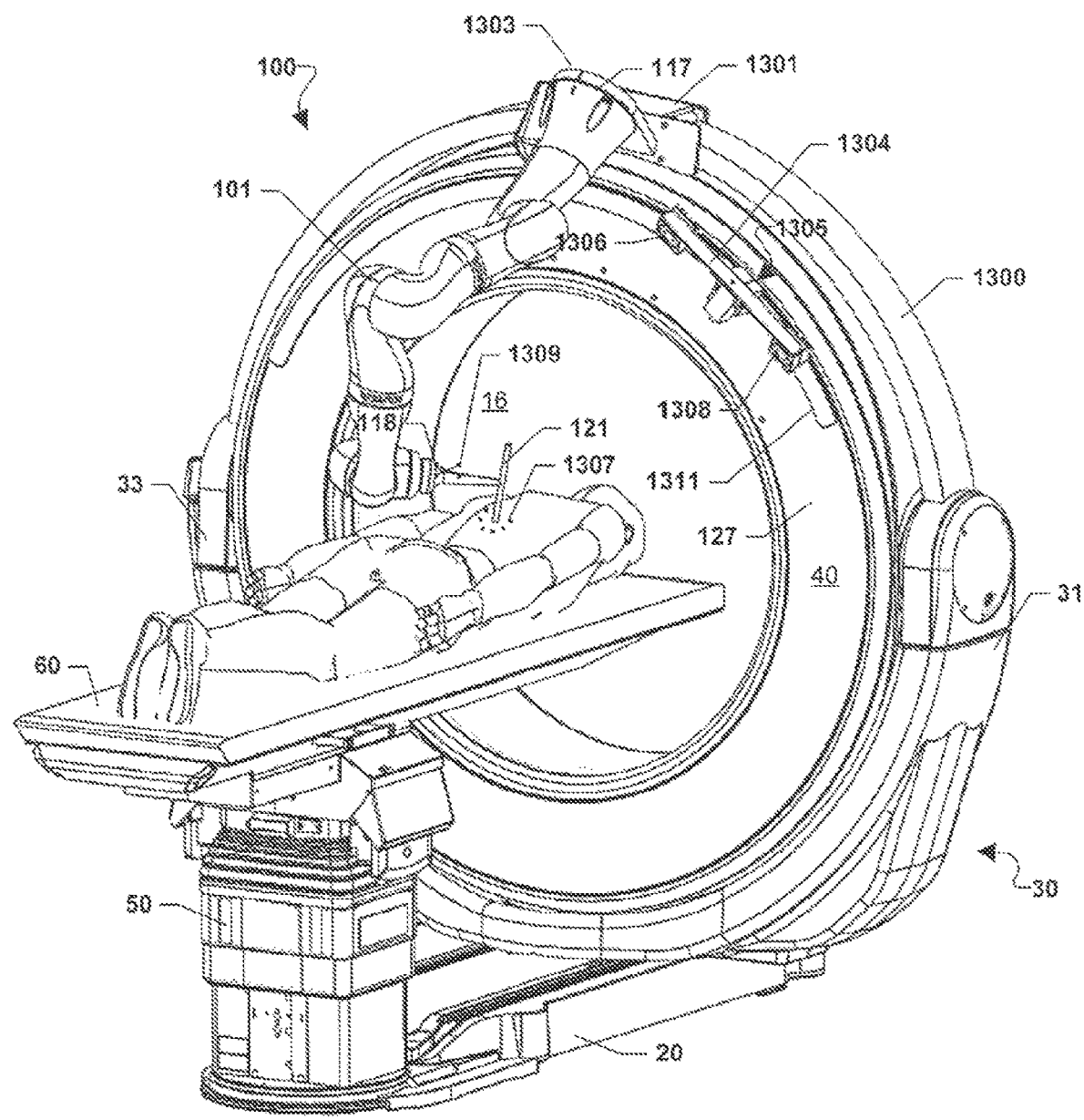
Figure 13B:
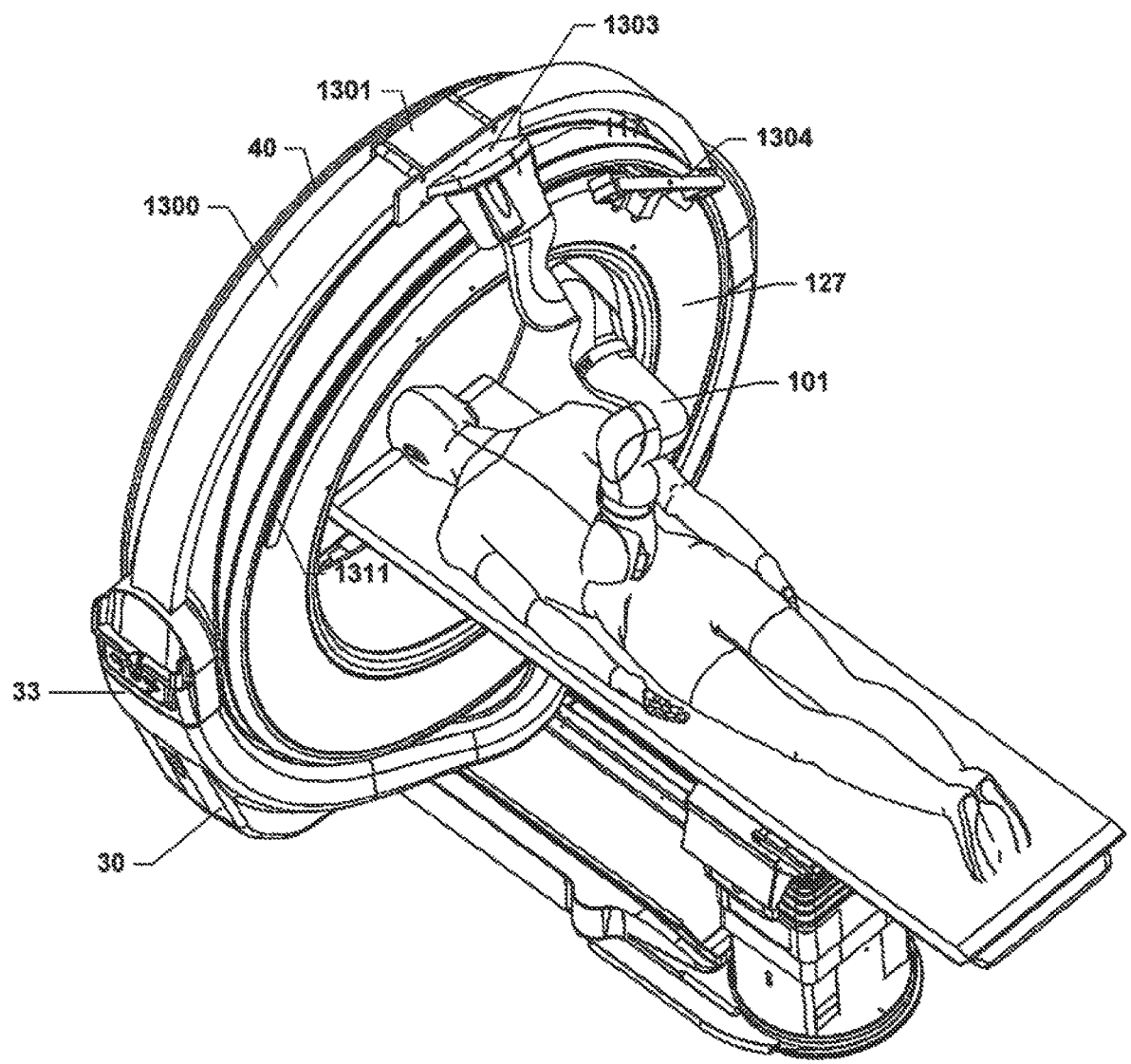
Figure 13C:
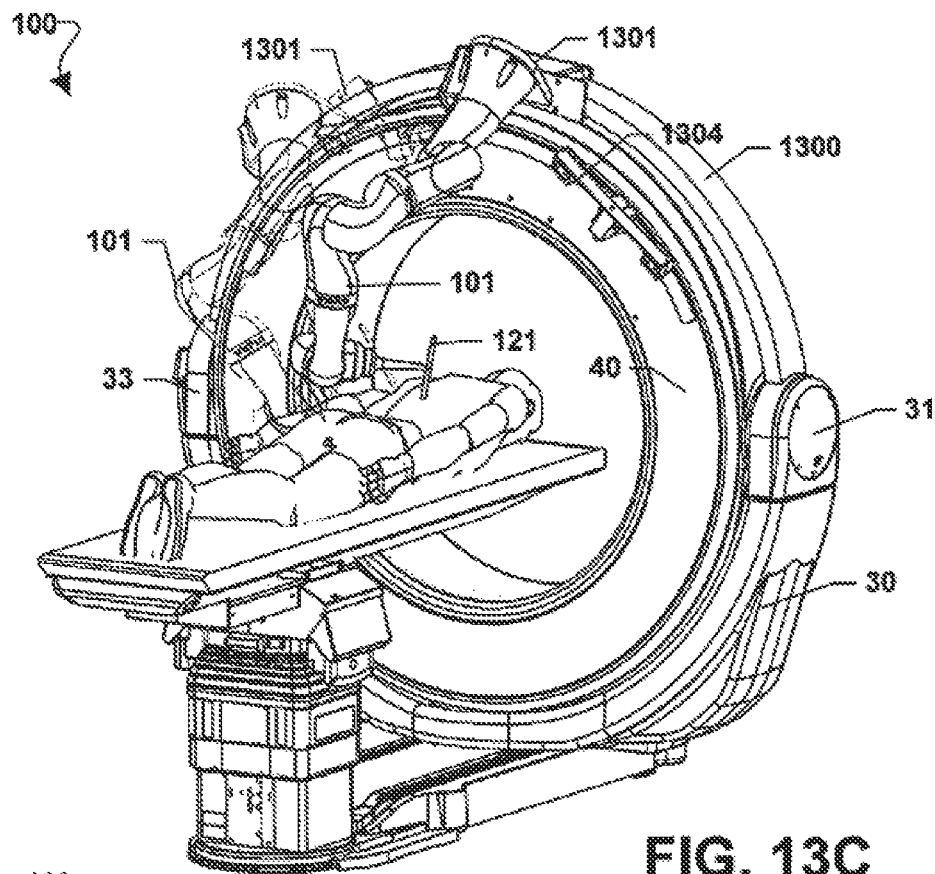
Figure 13D:
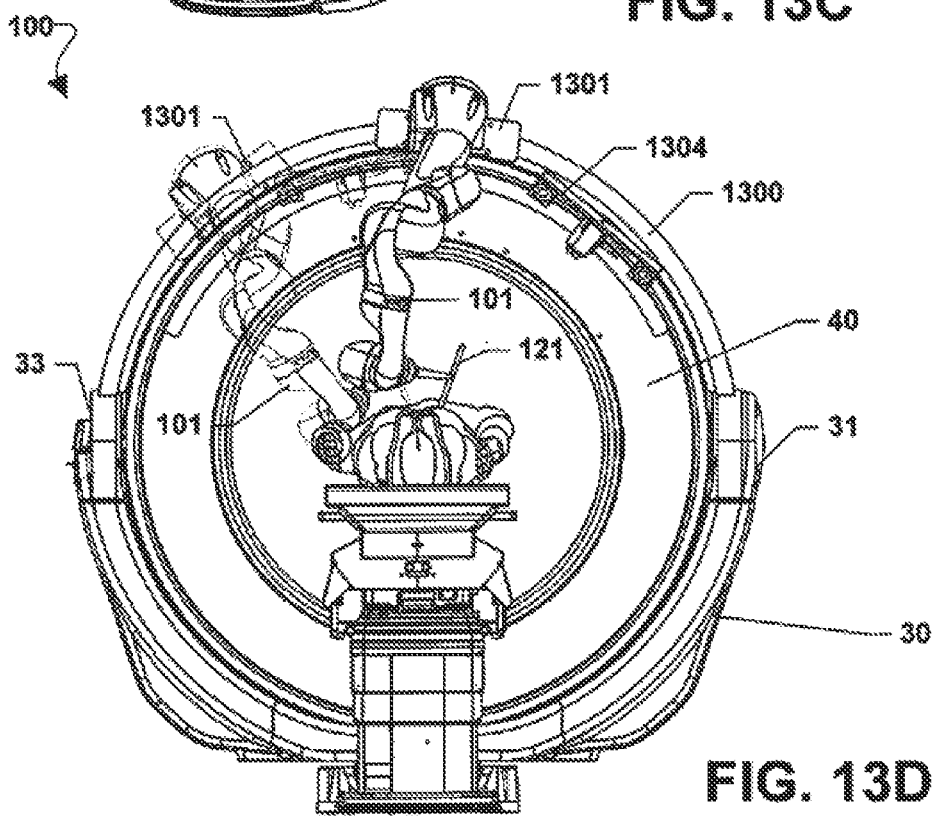

FIG. 13A-13D also illustrates a motion tracking apparatus 1305 which is similar to the motion tracking apparatus described above. In this embodiment, the motion tracking apparatus 1305 includes a stereoscopic optical sensor device 1304 that includes two or more IR cameras 1306, 1308 attached to the gantry 40 of the imaging device. The optical sensor device 1304 may include one or more IR sources (e.g., diode ring(s)) that direct IR radiation into the surgical field, where the IR radiation may be reflected by markers and received by the cameras 1306, 1308. As shown in FIG. 13A, a plurality of markers 1307 may be attached to the patient to form a "reference arc" that enables the cameras 1306, 1308 to track the patient. The optical sensor device 1305 may include a two-axis robotic system to enable the cameras 1306, 1308 to tilt and pan (i.e., rotate up-and-down and side-to-side) such that the reference arc on the patient may be maintained in the center of the cameras' field of view. A second set of markers 1309 may be attached to the second end 119 of the robotic arm 101 or to the end effector 121 to enable the tracking system to track the end effector 121. The second set of markers 1309 preferably comprises four or more non-coplanar markers in a fixed, known geometric relationship with each other and to the end effector 121, which enables both the position (x, y, z) and the orientation (yaw, pitch, roll) of the end effector 121 to be fully resolved. Similar sets of markers may be provided on any instruments or other objects brought into the surgical field to allow these objects to be tracked.

In the embodiment of FIGS. 13A-13D, the optical sensor device 1304 is mounted to the first (i.e., front) side 127 of the gantry 40 via a second support member 1311. The second support member 1311 may be a curved (e.g., semicircular) rail that may be attached to an upper portion of the gantry 40 to enable the cameras 1306, 1308 to look down into the surgical field. The optical sensor device 1304 may be movable to different positions along the second support member 1311, either manually or using a drive system. This may provide flexibility so that the robotic arm 101 may be translated to any location on support member 1300 while the optical sensor device 1304 may be translated to one side or the other of the robotic arm axis so that the cameras 1306, 1308 may remain pointed down into the surgical field without being occluded by the end of the robotic arm 101. Other motion tracking apparatuses, such as the apparatus 129 described above with reference to FIGS. 1A-12B, could be utilized in the system of FIGS. 13A-13D.

FIGS. 14A-14C illustrate an alternative embodiment of a system 100 for performing robotically-assisted surgery that includes at least one robotic arm 101 mounted to an imaging system 1400. In this embodiment, the imaging system 1400 includes an O-shaped imaging gantry 1401 that is mounted to a support structure 1403 in a cantilevered fashion. The imaging system 1400 may be an x-ray imaging system that may be used to obtain 2D fluoroscopic images and/or 3D tomographic images of an object located within the bore 16 of the gantry. At least one of an x-ray source and an x-ray detector (not visible in FIGS. 14A-14C) may rotate around the interior of the gantry 1401 to obtain images of an object within the bore 16 from different projection angles. The support structure 1403 may comprise a mobile cart 1406 that is attached to one side of the gantry 1401 via an attachment mechanism 1405. The attachment mechanism 1405 may include one or more motorized systems that enable the gantry 1401 to translate and/or rotate with respect to at least a portion of the cart 1406. For example, in embodiments the gantry 1401 may be raised or lowered relative to the cart 1406 and/or may be translated over a limited range-of-motion along the z-axis (i.e., into and out of the page in FIG. 14A) relative to the cart 1406. In addition, in some embodiments the gantry 1401 may be rotated with respect to the cart 1406 along one or more axis. For example, the gantry 1401 may be tilted with respect to the cart 1406 about a horizontal axis extending through the attachment point between the gantry 1401 and cart 1406 and/or may have a "wag" rotation about a vertical axis with respect to the cart 1406.

One or more robotic arms 101 may be attached anywhere on the imaging system 1400 of FIGS. 14A-14C, such as on the gantry 1401, the cart 1406 or the attachment mechanism 1405. In an embodiment shown in FIGS. 14A-14C, the robotic arm 101 is attached to a support member 1407 which may be similar to the support member 1300 described above with reference to FIGS. 13A-13D. In this embodiment, the support member 1407 extends from the attachment mechanism 1405, although the support member 1407 may extend from any portion of the cart 1406. The support member 1407 in this embodiment is a semicircular segment that extends concentrically over an upper portion of the gantry 1401. The support member 1407 and the robotic arm 101 secured thereto may translate with the translation of the gantry 1401 along at least one axis (e.g., up and down translation) relative to the cart 1406. In embodiments, the gantry 1401 may be able to rotate (e.g., tilt) with respect to the cart 1406 without the support member 1407 and robotic arm 101 also rotating.

The robotic arm 101 may be attached to the support member 1407 using a bracket mechanism 1301 as described above. The bracket mechanism 1301 and robotic arm may be moved to any arbitrary position along the length of the support member 1407. In addition, the system may include a tracking system comprising an optical sensor device 1304 mounted to a side of the gantry 1401 via a second support member 1313, as is described above with reference to FIGS. 13A-13D. The optical sensor device 1304 may be moveable to different positions along the length of the second support member 1313, as described above. Other motion tracking apparatuses, such as the apparatus 129 described above with reference to FIGS. 1A-12B, could be utilized in the system of FIGS. 14A-14C.

FIGS. 15A-15D illustrate another alternative embodiment of a system 100 for performing robotically-assisted surgery that includes at least one robotic arm 101 mounted to an imaging system 1500. In this embodiment, the imaging system 1500 is a C-arm device that includes an x-ray source 1501 and a detector 1503 connected to one another by a C-shaped connecting member 1505. The C-shaped connecting member 1505 is coupled to a support structure 1507, which in this embodiment comprises a mobile cart 1509. An attachment mechanism 1511 attaches the C-shaped connecting member 1505 to the cart 1509 such that the attachment mechanism 1511 together with the source 1501, detector 1503 and C-shaped connecting member 1505 may be rotated in a first direction (i.e., into and out of the page in FIG. 15A) relative to the cart 1509. In some embodiments, the source 1501, detector 1503 and C-shaped connecting member 1505 may also rotate in a second direction (i.e., within the plane of the page in FIG. 15A) relative to the attachment mechanism 1511 and the cart 1509. As discussed above, the cart 1509 may be a mobile cart and may be used to move the entire imaging system 1500 to a desired position and orientation. The source 1501 and detector 1503 may be used to obtain x-ray images, such as 2D fluoroscopic images, of an object positioned between the source 1501 and detector 1503 from a variety of different projection angles.

One or more robotic arms 101 may be attached anywhere on the imaging system 1500 of FIGS. 15A-15D, such as the on the cart 1509, the attachment mechanism 1511 or the C-shaped connecting member 1505. In an embodiment shown in FIGS. 15A-15D, the robotic arm 101 is attached to a support member 1513 which may be similar to the support members 1300 and 1407 described above with reference to FIGS. 13A-13D and 14A-14C. In this embodiment, the support member 1513 extends from the cart 1509.

The support member 1513 in this embodiment is a curved (e.g., semicircular) segment that extends from the cart 1509 at least partially above the source 1501, detector 1503 and the C-shaped connecting member 1505. The support member 1513 may be concentric with the C-shaped connecting member 1505. The support member 1513 may be located such that the source 1501 and detector 1503 may freely rotate about one or more axes without contacting the support member 1513.

Figure 15A:
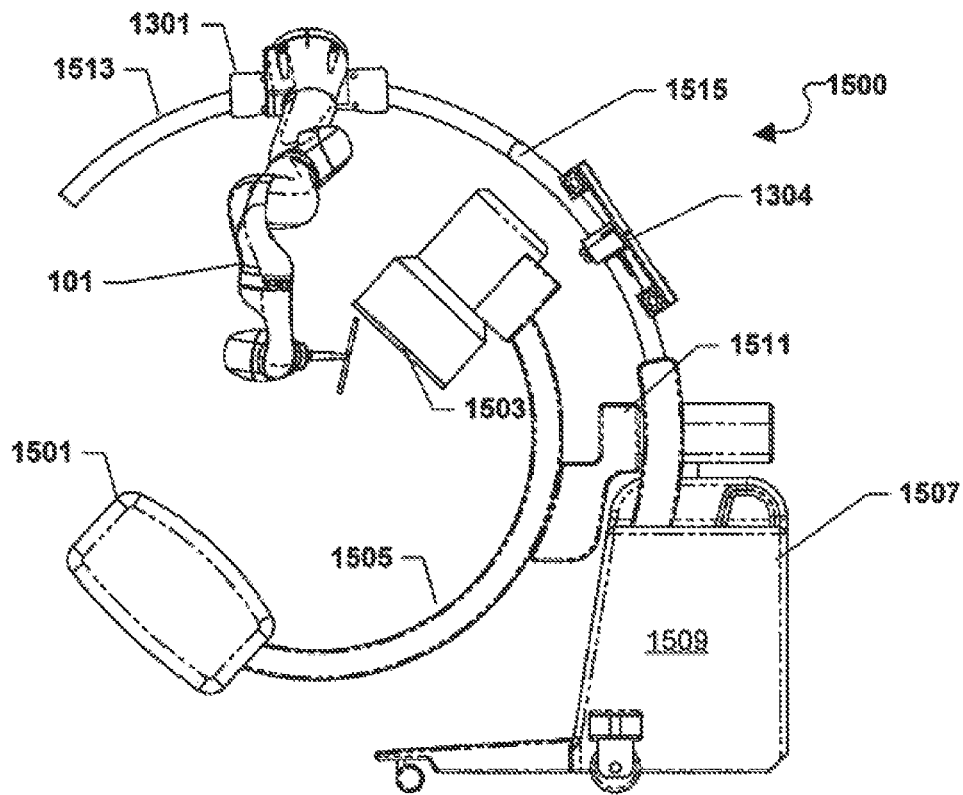
Figure 15B:
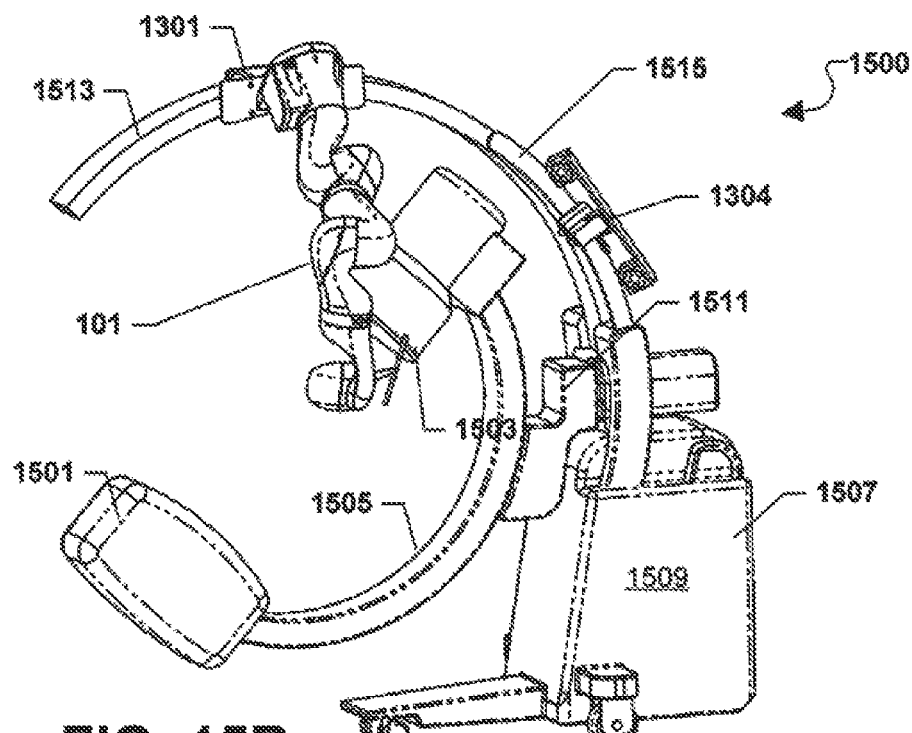
Figures 15C, 15D:
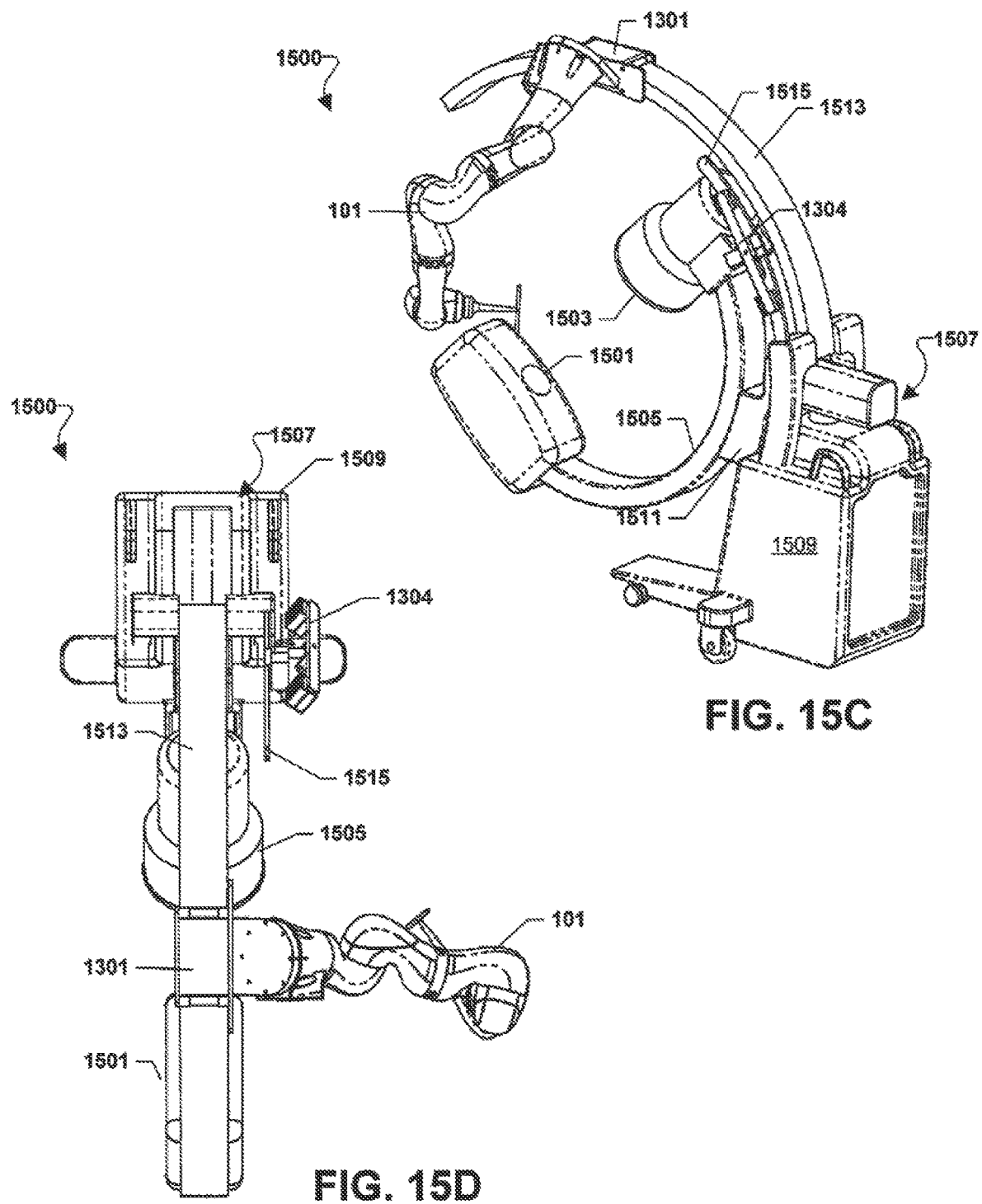

The robotic arm 101 may be attached to the support member 1513 using a bracket mechanism 1301 as described above. The bracket mechanism 1301 and robotic arm 101 may be moved to any arbitrary position along the length of the support member 1513. In addition, the system may include a tracking system comprising an optical sensor device 1304 mounted to a side of the gantry 1401 via a second support member 1515. The second support member 1515 may be a second curved (e.g., semicircular) segment that extends from the cart 1509 at least partially above the source 1501, detector 1503 and the C-shaped connecting member 1505. The second support member 1515 may extend parallel to support member 1513, as shown in FIGS. 15A-15C. In this embodiment, the second support member 1515 extends for a shorter length than support member 1513, although it will be understood that the second support member 1515 may extend for the same or a greater length than support member 1513. The optical sensor device 1304 may be moveable to different positions along the length of the second support member 1515, as described above. Alternately, both the robotic arm 101 and the optical sensor device 1304 may be mounted to the same support member (e.g., support member 1513). Also, other motion tracking apparatuses, such as the apparatus 129 described above with reference to FIGS. 1A-12B, could be utilized in the system of FIGS. 15A-15D.

FIG. 16 is a system block diagram of a computing device useful to perform functions of a processing control unit, such as controllers 105, 205 and 213 described above. While the computing device 1600 is illustrated as a laptop computer, a computing device providing the functional capabilities of the computer device 1600 may be implemented as a workstation computer, an embedded computer, a desktop computer or a handheld computer (e.g., tablet, a smartphone, etc.). A typical computing device may include a processor 1601 coupled to an electronic display 1604, a speaker 1606 and a memory 1602, which may be a volatile memory as well as a nonvolatile memory (e.g., a disk drive). When implemented as a laptop computer or desktop computer, the computing device 1600 may also include a floppy disc drive, compact disc (CD) or DVD disc drive coupled to the processor 1601. The computing device 1600 may include an antenna 1610, a multimedia receiver 1612, a transceiver 1618 and/or communications circuitry coupled to the processor 1601 for sending and receiving electromagnetic radiation, connecting to a wireless data link, and receiving data. Additionally, the computing device 1600 may include network access ports 1624 coupled to the processor for establishing data connections with a network (e.g., LAN coupled to a service provider network, etc.). A laptop computer or desktop computer 1600 typically also includes a keyboard 1614 and a mouse pad 1616 for receiving user inputs.

The foregoing method descriptions are provided merely as illustrative examples and are not intended to require or imply that the steps of the various embodiments must be performed in the order presented. As will be appreciated by one of skill in the art the order of steps in the foregoing embodiments may be performed in any order. Words such as "thereafter," "then," "next," etc. are not necessarily intended to limit the order of the steps; these words may be used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The hardware used to implement the various illustrative logics, logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored on as one or more instructions or code on a non-transitory computer-readable medium. The steps of a method or algorithm disclosed herein may be embodied in a processor-executable software module executed which may reside on a non-transitory computer-readable medium. Non-transitory computer-readable media includes computer storage media that facilitates transfer of a computer program from one place to another. A storage media may be any available media that may be accessed by a computer. By way of example, and not limitation, such non-transitory computer-readable storage media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of non-transitory computer-readable storage media. Additionally, the operations of a method or algorithm may reside as one or any combination or set of codes and/or instructions on a machine readable medium and/or computer-readable medium, which may be incorporated into a computer program product.

The preceding description of the disclosed aspects is provided to enable any person skilled in the art to make or use the present invention. Various modifications to these aspects will be readily apparent to those skilled in the art, and the generic principles defined herein may be applied to other aspects without departing from the scope of the invention. Thus, the present invention is not intended to be limited to the aspects shown herein but is to be accorded the widest scope consistent with the principles and novel features disclosed herein.

What is claimed is:

1. A system for performing robotically-assisted surgery, comprising:
a patient support coupled to a column for supporting a patient above a ground surface;
an imaging device including a support structure supporting an imaging gantry for linear movement along a longitudinal axis of the patient support, the imaging gantry supporting one or more imaging components arranged for movement relative to the support structure to obtain imaging data of the patient;
a motion tracking apparatus configured to track at least one of the patient and the imaging device; and
a robotic arm having a first end supporting an end effector and configured to extend into an imaging area of imaging gantry, and a second end operatively attached to the patient support, the robotic arm being configured to avoid collisions with the imaging device and with the patient in response to relative movement occurring between the imaging device and patient detected by the motion tracking apparatus.

2. The system of claim 1, wherein the robotic arm is further configured to maintain a pre-determined position and orientation of the end effector while the imaging device obtains the imaging data of the patient.

3. The system of claim 2, wherein the motion tracking apparatus is further configured to track the robotic arm.

4. The system of claim 3, wherein the motion tracking apparatus includes at least one marker operatively attached to the end effector of the robotic arm, and a sensing device configured to detect radiation emitted or reflected by the at least one marker to track the robotic arm.

5. The system of claim 4, wherein the motion tracking apparatus includes at least one marker fixed to the imaging device; and
wherein the sensing device is configured to detect radiation emitted or reflected by the at least one marker fixed to the imaging device to track the imaging device.

6. The system of claim 4, wherein the motion tracking apparatus is configured to detect movement of the end effector from the pre-determined position and orientation with respect to the patient.

7. The system of claim 6, further comprising a notification device configured to generate an alarm to alert a user in response to detecting movement of the end effector from the pre-determined position and orientation with respect to the patient.

8. The system of claim 6, wherein the imaging device is further configured to stop motion in response to detecting movement of the end effector from the pre-determined position and orientation with respect to the patient.

9. The system of claim 4, wherein the motion tracking apparatus includes at least one marker on the patient; and
wherein the sensing device is configured to detect radiation emitted or reflected by the at least one marker on the patient to track the patient.

10. The system of claim 9, wherein the robotic arm is further configured to maintain spaced relation from a boundary surface generated by the motion tracking apparatus sensing the at least one marker on the patient, the boundary surface encompassing at least a portion of the patient such that no portion of the robotic arm traverses the boundary surface.

11. The system of claim 1, wherein the imaging gantry of the imaging device is configured to tilt with respect to the support structure and the second end of the robotic arm operatively attached to the patient support.

12. The system of claim 11, wherein the support structure comprises a gimbal having a pair of arms that connect to opposite sides of the imaging gantry.

13. The system of claim 1, wherein a position of the second end of the robotic arm operatively attached to the patient support is adjustable by a user of the system.

14. The system of claim 13, wherein the patient support includes a longitudinal rail; and wherein the second end of the robotic arm is operatively attached to the longitudinal rail.

15. The system of claim 1, wherein the imaging device includes a base; and wherein the support structure is configured to linearly translate along the base to obtain the imaging data the patient positioned on the patient support.

16. The system of claim 15, wherein the column is operatively attached to the base of the imaging device.

17. The system of claim 15, wherein the patient support is configured to rotate relative to the base.

18. The system of claim 1, wherein the robotic arm, the imaging device, and the motion tracking apparatus operate in a common coordinate system.

19. The system of claim 1, wherein the one or more imaging components of the imaging device includes an x-ray source and an x-ray detector arranged such that at least one of the x-ray source and the x-ray detector is configured to rotate with respect to the support structure to obtain the imaging data of the patient from different projection angles.

20. The system of claim 1, wherein the column is configured to raise and lower a height of the patient support.

* * * * *